United States Patent
Chakravarthy et al.

(10) Patent No.: US 11,694,804 B2
(45) Date of Patent: *Jul. 4, 2023

(54) REDUCED POWER MACHINE LEARNING SYSTEM FOR ARRHYTHMIA DETECTION

(71) Applicant: Medtronic, Inc., Minneapolis, MN (US)

(72) Inventors: Niranjan Chakravarthy, Singapore (SG); Siddharth Dani, Minneapolis, MN (US); Tarek D. Haddad, Minneapolis, MN (US); Donald R. Musgrove, Minneapolis, MN (US); Andrew Radtke, Minneapolis, MN (US); Rodolphe Katra, Blaine, MN (US); Lindsay A. Pedalty, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 374 days.

This patent is subject to a terminal disclaimer.

(21) Appl. No.: 16/851,603

(22) Filed: Apr. 17, 2020

(65) Prior Publication Data

US 2020/0357519 A1    Nov. 12, 2020

Related U.S. Application Data

(60) Provisional application No. 62/843,717, filed on May 6, 2019.

(51) Int. Cl.
*G16H 50/20*    (2018.01)
*A61B 5/00*    (2006.01)
(Continued)

(52) U.S. Cl.
CPC ............ *G16H 50/20* (2018.01); *A61B 5/1116* (2013.01); *A61B 5/1118* (2013.01); *A61B 5/316* (2021.01);
(Continued)

(58) Field of Classification Search
CPC ........ G16H 50/20; G16H 50/30; G06N 20/00; G06N 5/02; G06N 5/04; A61B 5/25; A61B 5/1116; A61B 5/1118; A61B 5/7264
See application file for complete search history.

(56) References Cited

U.S. PATENT DOCUMENTS

| 4,458,691 A | 7/1984 | Netravali |
| 6,212,428 B1 | 4/2001 | Hsu et al. |

(Continued)

FOREIGN PATENT DOCUMENTS

| CN | 108030488 A | 5/2018 |
| EP | 1218060 B1 | 7/2002 |

(Continued)

OTHER PUBLICATIONS

U.S. Appl. No. 17/373,480, filed Jul. 12, 2021, naming inventors Chakravarthy et al.

(Continued)

*Primary Examiner* — John R Downey
(74) *Attorney, Agent, or Firm* — Shumaker & Sieffert, P.A.

(57) ABSTRACT

Techniques are disclosed for using feature delineation to reduce the impact of machine learning cardiac arrhythmia detection on power consumption of medical devices. In one example, a medical device performs feature-based delineation of cardiac electrogram data sensed from a patient to obtain cardiac features indicative of an episode of arrhythmia in the patient. The medical device determines whether the cardiac features satisfy threshold criteria for application of a machine learning model for verifying the feature-based delineation of the cardiac electrogram data. In response to determining that the cardiac features satisfy the threshold criteria, the medical device applies the machine learning model to the sensed cardiac electrogram data to verify that (Continued)

the episode of arrhythmia has occurred or determine a classification of the episode of arrhythmia.

22 Claims, 8 Drawing Sheets

(51) Int. Cl.
    *A61B 5/11*       (2006.01)
    *G16H 50/30*    (2018.01)
    *G06N 20/00*    (2019.01)
    *G06N 5/04*     (2023.01)
    *G06N 5/02*     (2023.01)
    *A61B 5/35*     (2021.01)
    *A61B 5/316*    (2021.01)

(52) U.S. Cl.
    CPC ............. *A61B 5/35* (2021.01); *A61B 5/7264* (2013.01); *G06N 5/02* (2013.01); *G06N 5/04* (2013.01); *G06N 20/00* (2019.01); *G16H 50/30* (2018.01)

(56) References Cited

U.S. PATENT DOCUMENTS

| | | | |
|---|---|---|---|
| 6,308,094 B1 | 10/2001 | Shusterman et al. | |
| 6,594,523 B1 | 7/2003 | Levine | |
| 8,103,346 B2 | 1/2012 | Mass et al. | |
| 8,521,281 B2 * | 8/2013 | Patel | A61B 5/361 607/30 |
| 9,183,351 B2 | 11/2015 | Shusterman | |
| 9,483,529 B1 | 11/2016 | Pasoi et al. | |
| 9,585,590 B2 | 3/2017 | McNair | |
| 9,743,890 B2 | 8/2017 | Lord et al. | |
| 9,775,559 B2 * | 10/2017 | Zhang | A61N 1/3702 |
| 10,463,269 B2 * | 11/2019 | Boleyn | A61B 5/6832 |
| 10,744,334 B2 | 8/2020 | Perschbacher et al. | |
| 11,355,244 B2 | 6/2022 | Haddad et al. | |
| 2002/0016550 A1 | 2/2002 | Sweeney et al. | |
| 2002/0123768 A1 | 9/2002 | Gilkerson et al. | |
| 2006/0247709 A1 | 11/2006 | Gottesman et al. | |
| 2009/0259269 A1 | 10/2009 | Brown | |
| 2010/0179444 A1 | 7/2010 | O'Brien et al. | |
| 2010/0268103 A1 | 10/2010 | McNamara et al. | |
| 2010/0280841 A1 | 11/2010 | Dong et al. | |
| 2011/0270109 A1 | 11/2011 | Zhang et al. | |
| 2012/0004563 A1 | 1/2012 | Kim et al. | |
| 2012/0209126 A1 | 8/2012 | Amos et al. | |
| 2013/0274524 A1 | 10/2013 | Dakka et al. | |
| 2013/0274624 A1 | 10/2013 | Mahanjan et al. | |
| 2014/0257063 A1 | 9/2014 | Ong et al. | |
| 2014/0378856 A1 | 12/2014 | Koike et al. | |
| 2015/0164349 A1 | 6/2015 | Gopalakrishnan et al. | |
| 2015/0216435 A1 | 8/2015 | Bokan et al. | |
| 2015/0265217 A1 | 9/2015 | Penders et al. | |
| 2016/0022164 A1 | 1/2016 | Brockway et al. | |
| 2016/0135706 A1 | 5/2016 | Sullivan et al. | |
| 2016/0192853 A1 | 7/2016 | Bardy et al. | |
| 2016/0220137 A1 * | 8/2016 | Mahajan | A61B 5/316 |
| 2016/0232280 A1 | 8/2016 | Apte et al. | |
| 2017/0095673 A1 | 4/2017 | Ludwig et al. | |
| 2017/0105683 A1 | 4/2017 | Xue | |
| 2017/0156592 A1 | 6/2017 | Fu | |
| 2017/0196458 A1 | 7/2017 | Ternes et al. | |
| 2017/0265765 A1 | 9/2017 | Baumann et al. | |
| 2017/0290550 A1 | 10/2017 | Perschbacher et al. | |
| 2017/0347894 A1 | 12/2017 | Bhushan et al. | |
| 2017/0354365 A1 | 12/2017 | Zhou | |
| 2018/0008976 A1 | 3/2018 | Okazaki | |
| 2018/0089763 A1 | 3/2018 | Okazaki | |
| 2018/0146874 A1 | 5/2018 | Walker et al. | |
| 2018/0146929 A1 | 5/2018 | Joo et al. | |
| 2018/0206721 A1 | 7/2018 | Zhang | |
| 2018/0233227 A1 | 8/2018 | Galloway et al. | |
| 2018/0272147 A1 | 9/2018 | Freeman et al. | |
| 2018/0279891 A1 | 10/2018 | Miao et al. | |
| 2018/0310892 A1 | 11/2018 | Perschbacher et al. | |
| 2019/0008461 A1 * | 1/2019 | Gupta | G16H 50/50 |
| 2019/0029552 A1 * | 1/2019 | Perschbacher | A61N 1/39622 |
| 2019/0038148 A1 | 2/2019 | Valys et al. | |
| 2019/0038149 A1 * | 2/2019 | Gopalakrishnan | A61B 5/7264 |
| 2019/0090774 A1 | 3/2019 | Yang et al. | |
| 2019/0122097 A1 | 4/2019 | Shibahara et al. | |
| 2019/0209022 A1 | 7/2019 | Sobol et al. | |
| 2019/0272920 A1 | 9/2019 | Teplitzky | |
| 2019/0275335 A1 * | 9/2019 | Volpe | A61N 1/3625 |
| 2019/0328251 A1 | 10/2019 | Jin | |
| 2019/0343415 A1 | 11/2019 | Saha et al. | |
| 2019/0365342 A1 | 12/2019 | Ghaffarzadegan et al. | |
| 2019/0378620 A1 | 12/2019 | Saren | |
| 2020/0100693 A1 * | 4/2020 | Velo | A61B 5/746 |
| 2020/0108260 A1 | 4/2020 | Haddad et al. | |
| 2020/0178825 A1 | 6/2020 | Weijia et al. | |
| 2020/0288997 A1 * | 9/2020 | Shute | A61B 5/7246 |
| 2020/0352462 A1 | 11/2020 | Pedalty et al. | |
| 2020/0352466 A1 | 11/2020 | Chakravarthy et al. | |
| 2020/0352521 A1 | 11/2020 | Chakravarthy et al. | |
| 2020/0353271 A1 | 11/2020 | Dani et al. | |
| 2020/0357517 A1 | 11/2020 | Haddad et al. | |
| 2020/0357518 A1 | 11/2020 | Musgrove et al. | |
| 2020/0357519 A1 | 11/2020 | Chakravarthy et al. | |
| 2021/0137384 A1 | 5/2021 | Robinson et al. | |
| 2021/0169736 A1 | 6/2021 | Wijshoff et al. | |
| 2021/0204858 A1 | 7/2021 | Attia et al. | |
| 2021/0338134 A1 | 11/2021 | Chakravarthy et al. | |
| 2021/0338138 A1 | 11/2021 | Pedalty et al. | |
| 2021/0343416 A1 | 11/2021 | Chakravarthy et al. | |
| 2021/0345865 A1 | 11/2021 | Spillinger et al. | |

FOREIGN PATENT DOCUMENTS

| | | |
|---|---|---|
| EP | 2427105 A1 | 3/2012 |
| WO | 2010129447 A1 | 11/2010 |
| WO | 2013/160538 A1 | 10/2013 |
| WO | 2017072250 A1 | 5/2017 |
| WO | 2017091736 A1 | 6/2017 |
| WO | 2018119316 A1 | 6/2018 |
| WO | 2020049267 A1 | 3/2020 |

OTHER PUBLICATIONS

U.S. Appl. No. 17/377,785, filed Jul. 16, 2021, Pedalty et al.
U.S. Appl. No. 17/389,831, filed Jul. 30, 2021, by Haddad et al.
U.S. Appl. No. 17/383,170, filed Jul. 22, 2021, by Haddad et al.
Isin et al., "Cardiac Arrhythmia Detection Using Deep Learning," Procedia Computer Science vol. 120, 2017 (Applicant points out, in accordance with MPEP 609.04(a), that the year of publication, 2017, is sufficiently earlier than he effective U.S. filing date, so that the particular month of publication is not in issue.) pp. 268-275.
Arrobo et al., "An Innovative Wireless Cardiac Rhythm Management (iCRM) System," Computer Science, 2014 Wireless Telecommunications Symposium, Jun. 2014, 5 pp.
Swerdlow et al., "Troubleshooting Implanted Cardioverter Defibrillator Sensing Problems I," Advances in Arrhythmia and Electrophysiology, vol. 7, No. 6, Dec. 2014, pp. 1237-1261.
Wartzek et al., "ECG on the Road: Robust and Unobtrusive Estimation of Heart Rate," IEEE Transactions on Biomedical Engineering, vol. 58, No. 11, Nov. 2011, pp. 3112-3120.
U.S. Appl. No. 17/377,763, filed Jul. 16, 2021, naming inventors Chakravarthy et al.
Bresnick, "Machine Learning Algorithm Outperforms Cardiologists Reading EKGs," Health IT Analytics, Jul. 12, 2017, 5 pp.
Office Action from U.S. Appl. No. 16/850,699 dated Jul. 28, 2022, 22 pp.
Prosecution History from U.S. Appl. No. 17/373,480, dated Feb. 22, 2022 through Sep. 6, 2022, 52 pp.
Prosecution History from U.S. Appl. No. 17/377,763, dated Oct. 13, 2021 through Aug. 5, 2022, 91 pp.
Andersen et al., "A Deep Learning Approach for Real-Time Detection of Atrial Fibrillation," Expert Systems with Applications, vol. 114, Aug. 14, 2018, pp. 465-473.

(56) References Cited

OTHER PUBLICATIONS

Madani et al., "Fast and Accurate View Classification of Echocardiograms Using Deep Learning," Nature Partner Journals, vol. 1, No. 6, Mar. 21, 2018, 8 pp.
Schirrmeister et al., "Deep learning with convolutional neural networks for brain mapping and decoding of movement-related information from the human EEG," arXiv:170.05051v1, Mar. 16, 2017, 58 pp.
U.S. Appl. No. 16/850,833, filed Apr. 16, 2020 by Dani et al.
U.S. Appl. No. 16/851,500, filed Apr. 17, 2020 by Musgrove et al.
International Search Report and Written Opinion of International Application No. PCT/US2020/028978, dated Jul. 27, 2020, 14 pp.
"Classify ECG Signals Using Long Short-Term Memory Networks," MATLAB, retrieved from https://www.mathworks.com/help/signal/examples/classify-ecg-signals-using-long-short-term-memory-networks.html, Nov. 2, 2018, 19 pp.
"Visualize Features of a Convolutional Neural Network," MATLAB & Simulink, Mar. 15, 2018, 9 pp.
Fawaz et al., "Deep learning for time series classification: a review," Irirmas, Universite Haute Alsace, Dec. 7, 2018, 53 pp.
Kelwade et al., "Prediction of Cardiac Arrhythmia using Artificial Neural Network," International Journal of Computer Applications (0975-8887), vol. 115—No. 20, Apr. 2015, 6 pp.
Lau et al., "Connecting the Dots: From Big Data to Healthy Heart," Circulation, vol. 134, No. 5, Aug. 2, 2017, 5 pp.
Schwab et al., "Beat by Beat: Classifying Cardiac Arrhythmias with Recurrent Neural Networks," 2017 Computing in Cardiology (CinC), vol. 44, Oct. 24, 2017, 4 pp.
U.S. Appl. No. 62/843,738, filed May 6, 2019, 2019 by Chakravarthy et al.
U.S. Appl. No. 16/832,732, filed Mar. 27, 2020 by Chakravarthy et al.
U.S. Appl. No. 16/845,996, filed Apr. 10, 2020 by Haddad et al.
U.S. Appl. No. 16/593,739, filed Oct. 4, 2019 by Haddad et al.
U.S. Appl. No. 62/843,730, filed May 6, 2019 by Pedalty et al.
"Visualize Features of a Convolutional Neural Network," MATLAB & Simulink, retrieved from https://www.mathworks.com/help/deeplearning/examples/visualize-features-of-a-convolutional-neural-network.html, Sep. 11, 2019, 7 pp.
International Preliminary Report on Patentability from International Application No. PCT/US2020/028978, dated Nov. 18, 2021, 8 pp.
Response to Office Action dated Oct. 13, 2021, from U.S. Appl. No. 17/377,763, filed Jan. 11, 2022, 17 pp.
U.S. Appl. No. 16/850,699, filed Apr. 16, 2020, by Chakravarthy et al.
U.S. Appl. No. 16/850,749, filed Apr. 16, 2020, by Pedalty et al.
Advisory Action from U.S. Appl. No. 17/373,480 dated Nov. 14, 2022, 3 pp.
Anonymous, "Receiver Operating Characteristic—Wikipedia," Mar. 20, 2019, Retrieved from the Internet: URL: https://en.wikipedia.org/w/index.php?title=Receiver_operating_characteristic&oldis=888671034#History, 12 pp.
Chen et al., "Electrocardiogram Recognition Based on Variational AutoEncoder," Machine Learning and Biometrics, IntechOpen, Aug. 29, 2018, pp. 71-90.
Habibzadeh et al., "On Determining the Most Appropriate Test Cut-Off Value: the Case of Tests with Continuous Results," Biochemia Medica, Oct. 15, 2016, pp. 297-307.
Office Action from U.S. Appl. No. 17/373,480 dated Jan. 10, 2023, 10 pp.
Response to Final Office Action dated Sep. 6, 2022 from U.S. Appl. No. 17/373,480, filed Nov. 2, 2022, 13 pp.
Witten et al., "Data mining: Practical Machine Learning Tools and Techniques," Third Edition, Morgan Kaufmann, Feb. 3, 2011, 665 pp.
Response to Office Action dated Jan. 10, 2023 from U.S. Appl. No. 17/373,480, filed Apr. 25, 2023, 4 pp.

\* cited by examiner

REDUCED POWER MACHINE LEARNING SYSTEM FOR ARRHYTHMIA DETECTION

This application claims the benefit of U.S. Provisional Application No. 62/843,717 which was filed on May 6, 2019. The entire content of Application No. 62/843,717 is incorporated herein by reference.

FIELD

This disclosure generally relates to medical devices and, more particularly, to medical devices configured to detect arrhythmias.

BACKGROUND

Malignant tachyarrhythmia, for example, ventricular fibrillation, is an uncoordinated contraction of the cardiac muscle of the ventricles in the heart, and is the most commonly identified arrhythmia in cardiac arrest patients. If this arrhythmia continues for more than a few seconds, it may result in cardiogenic shock and cessation of effective blood circulation. Consequently, sudden cardiac death (SCD) may result in a matter of minutes.

In patients with a high risk of ventricular fibrillation, the use of an implantable medical device (IMD), such as an implantable cardioverter defibrillator (ICD), has been shown to be beneficial at preventing SCD. An ICD is a battery powered electrical shock device, that may include an electrical housing electrode (sometimes referred to as a can electrode), that is typically coupled to one or more electrical lead wires placed within the heart. If an arrhythmia is sensed, the ICD may send a pulse via the electrical lead wires to shock the heart and restore its normal rhythm. Some ICDs have been configured to attempt to terminate detected tachyarrhythmias by delivery of anti-tachycardia pacing (ATP) prior to delivery of a shock. Additionally, ICDs have been configured to deliver relatively high magnitude post-shock pacing after successful termination of a tachyarrhythmia with a shock, in order to support the heart as it recovers from the shock. Some ICDs also deliver bradycardia pacing, cardiac resynchronization therapy (CRT), or other forms of pacing.

Other types of medical devices may be used for diagnostic purposes. For instance, an implanted or non-implanted medical device may monitor a patient's heart. A user, such as a physician, may review data generated by the medical device for occurrences of cardiac arrhythmias, e.g., atrial or ventricular tachyarrhythmia, or asystole. The user may diagnose a medical condition of the patient based on the identified occurrences of the cardiac arrhythmias.

SUMMARY

In accordance with the techniques of the disclosure, a medical device system is set forth herein that uses feature delineation and machine learning to perform cardiac arrhythmia detection and classification. Specifically, a medical device system as described herein may use feature delineation to make a preliminary detection of cardiac arrhythmia in a patient and only use a machine learning model to verify the episodes of cardiac arrhythmia detected by the feature delineation or classify such episodes detected by feature delineation as being a particular type of cardiac arrhythmia.

As described herein, feature delineation refers to the use of features obtained through signal processing for use in detecting or classifying an episode cardiac arrhythmia. Typically, feature delineation involves the use of engineered rules to identify or extract features in cardiac electrogram data, measure characteristics of such features, and use the measurements to detect or classify arrhythmia. For example, feature delineation may be used to identify features such as R-waves, QRS complexes, P-waves, T-waves, rates of such features, intervals between such features, feature morphology, widths or amplitudes of such features, or other or other types of cardiac features or characteristics of such features not expressly described herein. Feature delineation may include feature extraction, signal filtering, peak detection, refractory analysis, or other types of signal processing, feature engineering, or detection rule development. Feature delineation algorithms may be optimized for real-time, embedded, and low-power applications, such as for use by an implantable medical device. However, feature delineation algorithms may require expert design and feature engineering to accurately detect arrhythmia in a patient.

In contrast to feature delineation techniques for cardiac arrhythmia detection and classification, machine learning techniques may be used for cardiac arrhythmia detection and classification. As described herein, machine learning refers the use of a machine learning model, such as a neural network or deep-learning model, that is trained on training datasets to detect cardiac arrhythmia from cardiac electrogram data. Machine learning techniques may be contrasted from feature delineation in that feature delineation relies on signal processing, which machine learning systems may "learn" underlying features present in cardiac electrogram data indicative of an episode of arrhythmia without requiring knowledge or understanding of the relationship between the features and the episode of arrhythmia on behalf of the system designer.

In one example, a medical device, such as an IMD, senses cardiac electrogram data of a patient. The medical device performs feature-based delineation of the cardiac electrogram data to obtain cardiac features indicative of an episode of arrhythmia in the patient. The medical device determines whether the cardiac features satisfy threshold criteria for application of a machine learning model for verifying the feature-based delineation of the cardiac electrogram data. In response to determining that the cardiac features satisfy the threshold criteria for application of the machine learning model, the medical device applies the machine learning model to the sensed cardiac electrogram data to, e.g., verify that the episode of arrhythmia has occurred in the patient or to detect one or more other types of arrhythmia that have occurred in the patient.

In another example, the medical device compares first cardiac features of the cardiac electrogram data to cardiac features defined by entries of an arrhythmia dictionary. In response to determining that the first cardiac features of the cardiac electrogram data are not similar to the cardiac features defined by entries of an arrhythmia dictionary, the medical device applies a machine learning model to determine a classification of an episode of arrhythmia demonstrated by the first cardiac features. The medical device may store the determined arrhythmia classification and cardiac features as a new entry in the arrhythmia dictionary so as to build the arrhythmia dictionary. Upon subsequently detecting, via feature delineation, second cardiac features that are similar to the first cardiac features, the medical device determines that the second cardiac features are indicative of an episode of arrhythmia of the same classification as the episode of arrhythmia demonstrated by the first cardiac features.

The techniques of the disclosure may provide specific improvements to the field of cardiac arrhythmia detection and classification by medical devices. For example, the techniques of the disclosure may use machine learning models for only the analysis of cardiac features that have been identified by feature delineation as likely presenting an episode of arrhythmia in the patient. By using machine learning models to verify arrhythmia detection in the patient, the techniques of the disclosure may increase the accuracy in arrhythmia detection. Further, by using low-power feature delineation to limit the use of computationally-complex, power-intensive machine learning models to only the most relevant patient data, the techniques of the disclosure may efficiently implement machine learning models to detect cardiac arrhythmia detection without adversely increasing the power usage and decreasing the battery life of such medical devices.

In one example, this disclosure describes a method comprising: sensing, by a medical device comprising processing circuitry and a storage medium, cardiac electrogram data of a patient; performing, by the medical device, feature-based delineation of the sensed cardiac electrogram data to obtain cardiac features present in the cardiac electrogram data and indicative of an episode of arrhythmia in the patient; determining, by the medical device and based on the feature-based delineation, that the cardiac features satisfy threshold criteria for application of a machine learning model for verifying that the episode of arrhythmia has occurred in the patient; in response to determining that the cardiac features satisfy the threshold criteria, applying, by the medical device, the machine learning model, trained using cardiac electrogram data for a plurality of patients, to the sensed cardiac electrogram data to verify, based on the machine learning model, that the episode of arrhythmia has occurred in the patient; and in response to verifying, by the machine learning model, that the episode of arrhythmia has occurred in the patient: generating, by the medical device, a report comprising an indication that the episode of arrhythmia has occurred in the patient and one or more of the cardiac features that coincide with the episode of arrhythmia; and outputting, by the medical device and for display, the report comprising the indication that the episode of arrhythmia has occurred in the patient and the one or more of the cardiac features that coincide with the episode of arrhythmia.

In another example, this disclosure describes a method comprising: sensing, by a medical device comprising processing circuitry and a storage medium, cardiac electrogram data of a patient; performing, by the medical device, feature-based delineation of the sensed cardiac electrogram data to obtain cardiac features present in the cardiac electrogram data; determining, by the medical device, a similarity of the obtained cardiac features to cardiac features of each entry of a plurality of entries of an arrhythmia dictionary of the medical device, wherein each entry of the plurality of entries of the arrhythmia dictionary comprises a classification of arrhythmia of a plurality of classifications of arrhythmia in the patient and cardiac features that demonstrate the classification of arrhythmia; in response to determining that the obtained cardiac features are not similar to the cardiac features of each entry of the plurality of entries of the arrhythmia dictionary, applying, by the medical device, a machine learning model, trained using cardiac electrogram data for a plurality of patients, to the sensed cardiac electrogram data to determine, based on the machine learning model, that an episode of arrhythmia of a first classification has occurred in the patient; and storing, by the medical device and in the arrhythmia dictionary, a first entry comprising the first classification of the episode of arrhythmia and the obtained cardiac features.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF DRAWINGS

Like reference characters refer to like elements throughout the figures and description.

DETAILED DESCRIPTION

Techniques are disclosed for the efficient use of machine learning methods for cardiac arrhythmia detection in medical devices. Feature delineation algorithms may use cardiac electrogram data sensed from a patient to perform, e.g., QRS detection and/or arrhythmia detection. Such feature delineation algorithms may be optimized for real-time, embedded, and low-power applications, such as for use by an implantable medical device. However, feature delineation algorithms may require expert design and feature engineering to accurately detect arrhythmias in a patient.

Machine learning methods for arrhythmia detection, such as deep-learning and artificial intelligence (AI), provide a flexible platform to develop algorithms with different objectives. For example, a machine learning system may, e.g., detect atrial fibrillation (AF), exclude episodes that exhibit no arrhythmia, etc., with a high degree of accuracy without the expert design and feature engineering required by cardiac arrhythmia algorithms such as feature delineation. However, machine learning systems may be computationally prohibitive for implementation in medical devices, such as IMDs or medical devices that operate on battery power. The frequent use of computationally expensive machine learning models on a medical device may affect battery longevity.

As described in detail herein, techniques, methods, systems, and devices are disclosed for physiologic, device-based and algorithm-based methods that condition the use of on-device machine learning systems to ensure efficient power usage. As set forth herein, a medical device system is described that allows for the use of in-device machine learning arrhythmia detection, such as deep-learning or AI, in a power-efficient manner so as to enable the use of machine learning arrhythmia detection by medical devices that perform short-term or long-term diagnostic analysis or monitoring.

Figure 1:
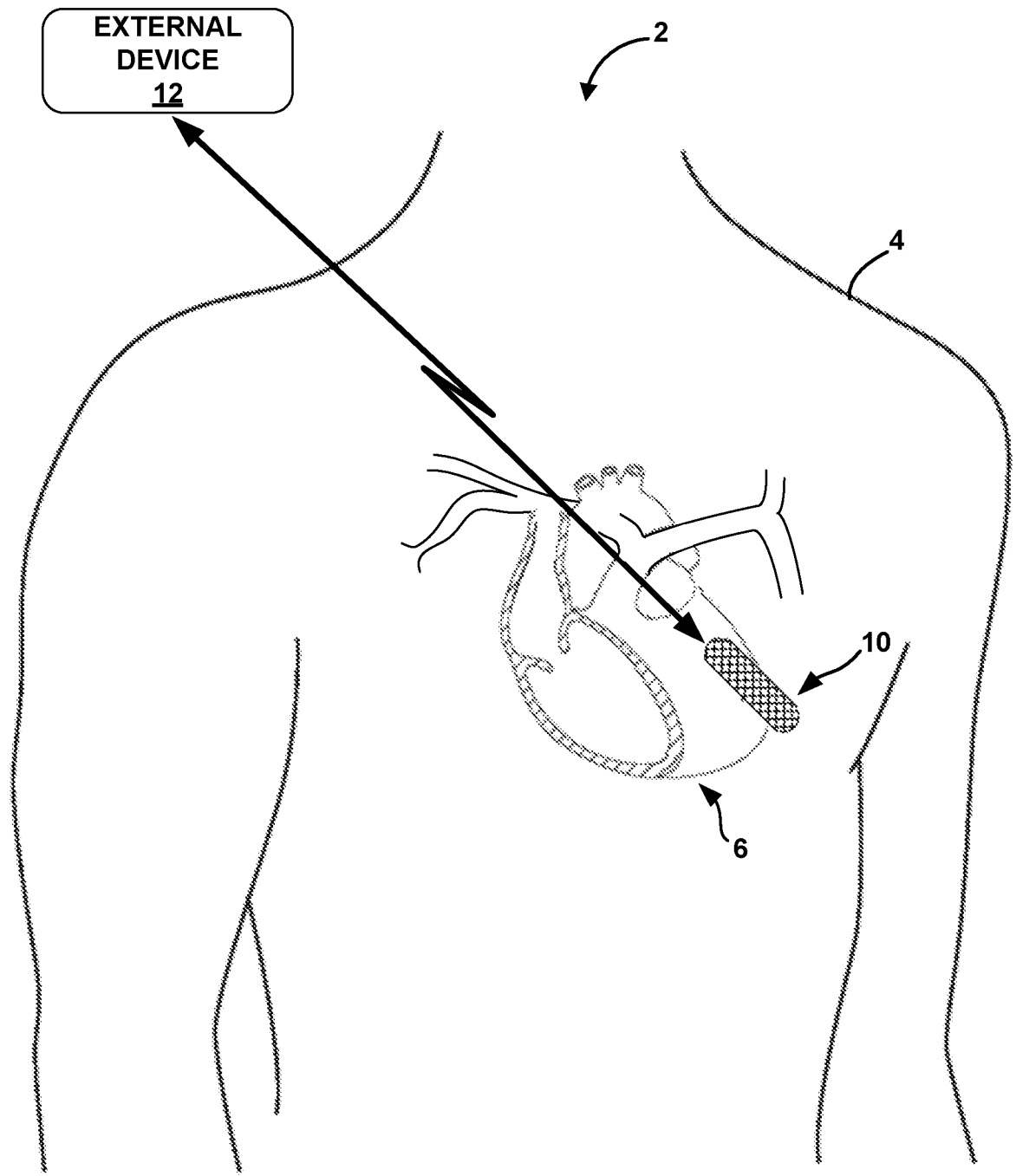
FIG. 1 is a conceptual drawing illustrating an example of a medical device system for predicting cardiac arrhythmia including a leadless implantable medical device and an external device in conjunction with a patient in accordance with the techniques of the disclosure.

FIG. 1 illustrates the environment of an example medical device system 2 in conjunction with a patient 4 and a heart 6, in accordance with an apparatus and method of certain examples described herein. The example techniques may be used with an IMD 10, which may be leadless and in wireless communication with external device 12, as illustrated in FIG. 1. In some examples, IMD 10 may be coupled to one or more leads. In some examples, IMD 10 may be implanted outside of a thoracic cavity of patient 4 (e.g., subcutaneously in the pectoral location illustrated in FIG. 1). IMD 10 may be positioned near the sternum near and/or just below the level of heart 6.

In some examples, IMD 10 may take the form of a Reveal LINQ™ Insertable Cardiac Monitor (ICM) or a Holter Heart Monitor, both available from Medtronic plc, of Dublin, Ireland. As discussed herein, the techniques of the disclosure may be performed by an implantable device, such as IMD 10.

In other examples, the techniques described herein may be performed by an external medical device such as external device 12 in addition to, or instead of IMD 10. Such an external medical device may be positioned externally to patient 4 (e.g., positioned on the skin of patient 4) and may carry out any or all of the functions described herein with respect to IMD 10. External device 12 may be a computing device configured for use in settings such as a home, clinic, or hospital, and may further be configured to communicate with IMD 10 via wireless telemetry. For example, external device 12 may be coupled to a remote patient monitoring system, such as Carelink®, available from Medtronic plc, of Dublin, Ireland. External device 12 may, in some examples, comprise a programmer, an external monitor, or a mobile device, such as a mobile phone, a "smart" phone, a laptop, a tablet computer, a personal digital assistant (PDA), etc. In some examples, external device 12 is a wearable electronic device, such as the SEEQ™ Mobile Cardiac Telemetry (MCT) system available from Medtronic plc, of Dublin, Ireland, or another type of wearable "smart" electronic apparel, such as a "smart" watch, "smart" patch, or "smart" glasses.

In some examples, a user, such as a physician, technician, surgeon, electro-physiologist, or other clinician, may interact with external device 12 to retrieve physiological or diagnostic information from IMD 10. In some examples, a user, such as patient 4 or a clinician as described above, may also interact with external device 12 to program IMD 10, e.g., select or adjust values for operational parameters of IMD 10. In some examples, external device 12 acts as an access point to facilitate communication with IMD 10.

A user, such as a physician, technician, surgeon, electro-physiologist, or other clinician, may interact with external device 12 to retrieve physiological or diagnostic information from IMD 10. A user may also interact with external device 12 to program IMD 10, e.g., select values for operational parameters of the IMD. External device 12 may include a processor configured to evaluate EGM and/or other sensed signals transmitted from IMD 10 to external device 12.

In any such examples, processing circuitry of medical device system 2 may transmit patient data, including cardiac electrogram data, for patient 4 to a remote computer (e.g., external device 12, or another device not depicted in FIG. 1). In some examples, processing circuitry of medical device system 2 may transmit a determination that patient 4 is undergoing an episode of cardiac arrhythmia such as an episode of bradycardia, tachycardia, atrial fibrillation, or ventricular fibrillation.

External device 12 may be a computing device (e.g., used in a home, ambulatory, clinic, or hospital setting) to communicate with IMD 10 via wireless telemetry. External device 12 may include or be coupled to a remote patient monitoring system, such as Carelink®, available from Medtronic plc, of Dublin, Ireland. In some examples, external device 12 may receive data, alerts, patient physiological information, or other information from IMD 10.

External device 12 may be used to program commands or operating parameters into IMD 10 for controlling its functioning (e.g., when configured as a programmer for IMD 10). In some examples, external device 12 may be used to interrogate IMD 10 to retrieve data, including device operational data as well as physiological data accumulated in IMD memory. Such interrogation may occur automatically according to a schedule and/or may occur in response to a remote or local user command. Programmers, external monitors, and consumer devices are examples of external devices 12 that may be used to interrogate IMD 10. Examples of communication techniques used by IMD 10 and external device 12 include radiofrequency (RF) telemetry, which may be an RF link established via Bluetooth, WiFi, or medical implant communication service (MICS). In some examples, external device 12 may include a user interface configured to allow patient 4, a clinician, or another user to remotely interact with IMD 10. In some such examples, external device 12, and/or any other device of medical device system 2, may be a wearable device, (e.g., in the form of a watch, necklace, or other wearable item).

Medical device system 2 is an example of a medical device system configured to perform cardiac arrhythmia detection, verification, and reporting. In accordance with the techniques of the disclosure, medical device system 2 implements machine learning arrhythmia detection and feature delineation to detect and classify cardiac arrhythmias in patient 4. Additional examples of the one or more other implanted or external devices may include an implanted, multi-channel cardiac pacemaker, ICD, IPG, leadless (e.g., intracardiac) pacemaker, extravascular pacemaker and/or ICD, or other IMD or combination of such IMDs configured to deliver CRT to heart 6, an external monitor, an external therapy delivery device such as an external pacing or electrical stimulation device, or a drug pump. In some examples, IMD 10 implements a machine learning system, such as neural network, a deep learning system, or other type of predictive analytics system.

Communication circuitry of each of the devices of medical device system 2 (e.g., IMD 10 and external device 12) may enable the devices to communicate with one another. In addition, although one or more sensors (e.g., electrodes) are described herein as being positioned on a housing of IMD 10, in other examples, such sensors may be positioned on a housing of another device implanted in or external to patient 4. In such examples, one or more of the other devices may include processing circuitry configured to receive signals from the electrodes or other sensors on the respective devices and/or communication circuitry configured to transmit the signals from the electrodes or other sensors to another device (e.g., external device 12) or server.

In accordance with the techniques of the disclosure, medical device system 2 uses feature delineation and machine learning to perform to cardiac arrhythmia detection and classification. Specifically, a medical device, such as IMD 10 or external device 12, uses feature delineation to make a preliminary detection of cardiac arrhythmia in patient 4. In some examples, the medical device applies a machine learning model to cardiac electrogram data of patient 2 to verify that feature delineation of the cardiac electrogram data has correctly detected an episode of cardiac arrhythmia. In some examples, the medical device applies a machine learning model to cardiac electrogram data of patient 2 to verify that feature delineation of the cardiac electrogram data has correctly classified an episode of cardiac arrhythmia as a particular type of arrhythmia. For ease of illustration, the following sections describe the techniques of the disclosure as being performed by IMD 10. However, the techniques of the disclosure may be performed by other types of medical devices, such as external device 12, or a combination of medical devices (e.g., IMD 10 and external device 12) operating in conjunction with one another.

In one example of the techniques of the disclosure, IMD 10 senses cardiac electrogram data of patient 4. IMD 10 performs feature-based delineation of the cardiac electrogram data to obtain cardiac features indicative of an episode of arrhythmia in patient 4. IMD 10 determines whether the cardiac features satisfy threshold criteria for application of a machine learning model for verifying the feature-based delineation of the cardiac electrogram data. In some examples, IMD 10 further determines that a noise of at least one of the cardiac features is less than a predetermined threshold. In some examples, IMD 10 further determines that the patient is in a first posture state of a plurality of posture states or a first activity state of a plurality of activity states. In response to determining that the cardiac features satisfy the threshold criteria, IMD 10 applies the machine learning model to the sensed cardiac electrogram data to, e.g., verify that the episode of arrhythmia has occurred in patient 4 or to detect one or more additional types of arrhythmia that have occurred in patient 4.

In one example of the techniques of the disclosure, IMD 10 may classify episodes of arrhythmia by comparing cardiac features coincident with the episode of arrhythmia with cardiac features of an arrhythmia dictionary maintained by IMD 10. IMD 10 compares first cardiac features of the cardiac electrogram data to cardiac features defined by an entry of the arrhythmia dictionary. For example, in response to determining that the first cardiac features of the cardiac electrogram data are similar to cardiac features defined by an entry of the arrhythmia dictionary, IMD 10 determines that the first cardiac features indicate that an episode of arrhythmia has occurred in patient 4 that is a classification defined by the matching entry within the arrhythmia dictionary.

As another example, in response to determining that the first cardiac features of the cardiac electrogram data are not similar to the cardiac features defined by any entries of the arrhythmia dictionary, IMD 10 applies a machine learning model to determine a classification of an episode of arrhythmia demonstrated by the first cardiac features. IMD 10 stores the determined arrhythmia classification and cardiac features as a new entry in the arrhythmia dictionary so as to build the arrhythmia dictionary. Upon subsequently detecting, via feature delineation, second cardiac features that are similar to cardiac features of an entry of the arrhythmia dictionary, IMD 10 determines that the second cardiac features are indicative of an episode of arrhythmia of the same classification as the episode of arrhythmia defined in the entry of the arrhythmia dictionary and including cardiac features that match the second cardiac features.

The techniques of the disclosure may provide specific improvements to the field of cardiac arrhythmia detection and classification by medical devices such as IMD 10. For example, the techniques of the disclosure may use machine learning models for only the analysis of cardiac electrogram signals that have been identified by feature delineation as likely presenting an episode of arrhythmia in the patient. By using machine learning models to verify arrhythmia detection in patient 4 performed by feature delineation, the techniques of the disclosure may leverage machine learning to increase the accuracy and flexibility of arrhythmia detection. Further, by using low-power feature delineation to limit the use of computationally-complex, power-intensive machine learning models to only the most relevant patient data, the techniques of the disclosure may efficiently implement machine learning models to detect cardiac arrhythmia detection without adversely increasing the power usage and decreasing the battery life of such medical devices.

Figure 2:
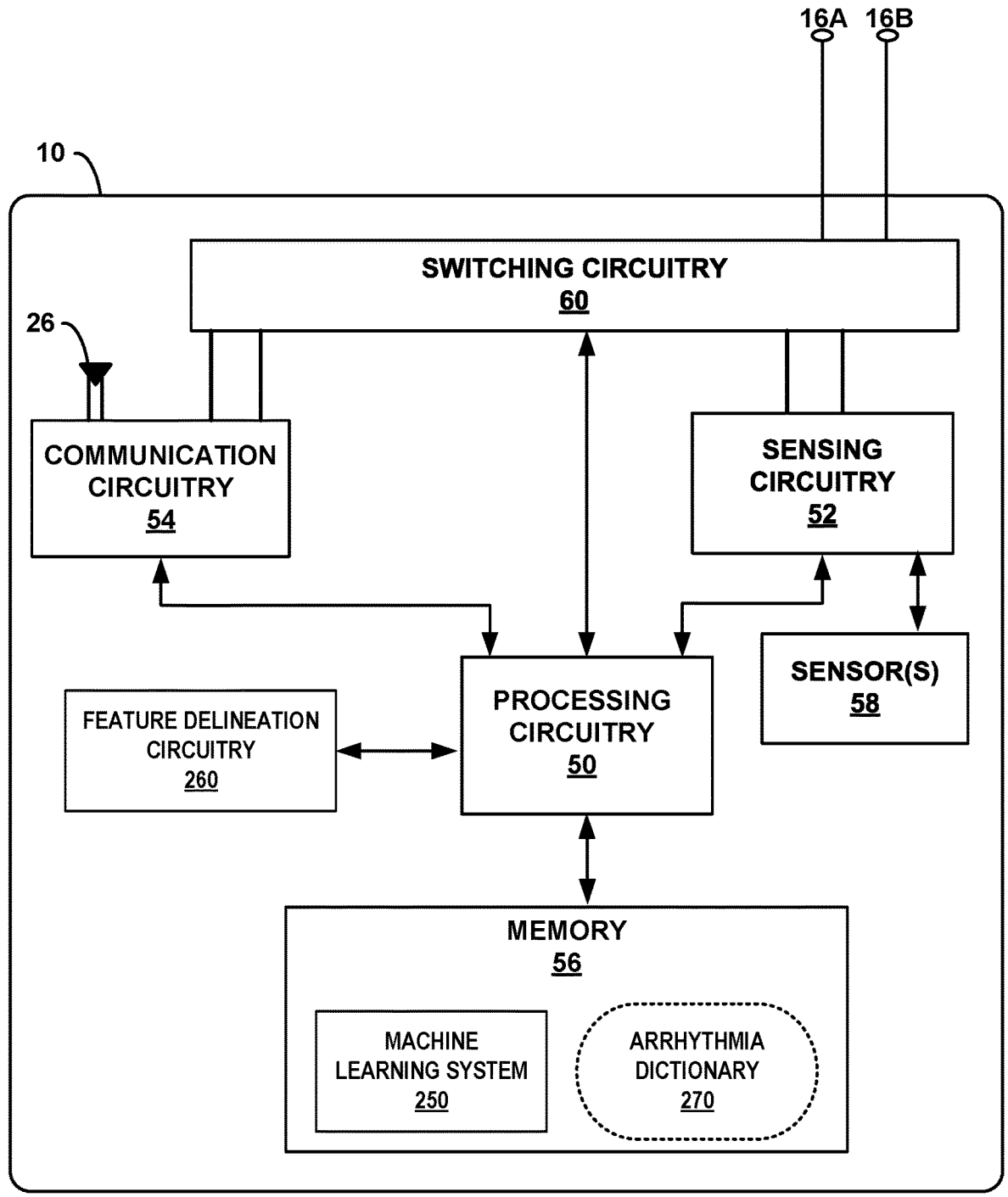
FIG. 2 is a block diagram illustrating an example of the implantable medical device of FIG. 1.

FIG. 2 is a block diagram illustrating an example of the implantable medical device of FIG. 1. As shown in FIG. 2, IMD 10 includes processing circuitry 50 sensing circuitry 52, communication circuitry 54, memory 56, sensors 58, switching circuitry 60, feature delineation circuitry 260, and electrodes 16A, 16B (hereinafter "electrodes 16"), one or more of which may be disposed within a housing of IMD 10. In some examples, memory 56 includes computer-readable instructions that, when executed by processing circuitry 50, cause IMD 10 and processing circuitry 50 to perform various functions attributed to IMD 10 and processing circuitry 50 herein. Memory 56 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital media.

Processing circuitry 50 may include fixed function circuitry and/or programmable processing circuitry. Processing circuitry 50 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof.

Sensing circuitry 52 and communication circuitry 54 may be selectively coupled to electrodes 16A, 16B via switching circuitry 60 as controlled by processing circuitry 50. Sensing circuitry 52 may monitor signals from electrodes 16A, 16B in order to monitor electrical activity of a heart of patient 4 of FIG. 1 and produce cardiac electrogram data for patient 4. In some examples, processing circuitry 50 performs feature delineation of the sensed cardiac electrogram data via feature delineation circuitry 260 to detect an episode of cardiac arrhythmia of patient 4. In some examples, processing circuitry 50 transmits, via communication circuitry 54, the cardiac electrogram data for patient 4 to an external device, such as external device 12 of FIG. 1. For example, IMD 10 sends digitized cardiac electrogram data to external device 12 of FIG. 1 for data processing or review by a clinician. In some examples, IMD 10 transmits one or more segments of the cardiac electrogram data in response to detecting, via feature delineation circuitry 260, an episode of arrhythmia. In another example, IMD 10 transmits one or more segments of the cardiac electrogram data in response to instructions from external device 12 (e.g., when patient 4 experiences one or more symptoms of arrhythmia and inputs a command to external device 12 instructing IMD 10 to upload the cardiac electrogram data for analysis by a monitoring center or clinician).

In some examples, IMD 10 includes one or more sensors 58, such as one or more accelerometers, microphones, and/or pressure sensors. Sensing circuitry 52 may monitor signals from sensors 58 and transmit patient data obtained from sensors 58, to an external device, such as external device 12 of FIG. 1, for analysis. In some examples, sensing circuitry 52 may include one or more filters and amplifiers for filtering and amplifying signals received from one or more of electrodes 16A, 16B and/or other sensors 58. In some examples, sensing circuitry 52 and/or processing circuitry 50 may include a rectifier, filter and/or amplifier, a sense amplifier, comparator, and/or analog-to-digital converter.

Communication circuitry 54 may include any suitable hardware, firmware, software or any combination thereof for communicating with another device, such as external device 12 or another medical device or sensor, such as a pressure sensing device. Under the control of processing circuitry 50, communication circuitry 54 may receive downlink telemetry from, as well as send uplink telemetry to, external device 12 or another device with the aid of an internal or external antenna, e.g., antenna 26. In some examples, communication circuitry 54 may communicate with external device 12. In addition, processing circuitry 50 may communicate with a networked computing device via an external device (e.g., external device 12) and a computer network, such as the Medtronic CareLink® Network developed by Medtronic, plc, of Dublin, Ireland.

A clinician or other user may retrieve data from IMD 10 using external device 12, or by using another local or networked computing device configured to communicate with processing circuitry 50 via communication circuitry 54. The clinician may also program parameters of IMD 10 using external device 12 or another local or networked computing device. In some examples, the clinician may select one or more parameters defining how IMD 10 senses cardiac electrogram data of patient 4.

One or more components of IMD 10 may be coupled a power source (not depicted in FIG. 2), which may include a rechargeable or non-rechargeable battery positioned within a housing of IMD 10. A non-rechargeable battery may be selected to last for several years, while a rechargeable battery may be inductively charged from an external device, e.g., on a daily or weekly basis.

In accordance with the techniques of the disclosure, processing circuitry 50 senses, with sensing circuitry 52 and via electrodes 16, cardiac electrogram data of patient 4. In some examples, the cardiac electrogram data is an ECG for patient 4. Processing circuitry 50 performs feature delineation of the cardiac electrogram data via feature delineation circuitry 260 to obtain one or more cardiac features present in the cardiac electrogram data. Feature delineation circuitry 260 may further make a preliminary detection of an episode of arrhythmia. In some examples, feature delineation circuitry 260 includes circuitry configured to perform one or more of QRS detection, refractory processing, noise processing, or delineation of the cardiac electrogram data. For example, feature delineation circuitry 260 receives a raw signal from via sensing circuitry 50 and/or sensors 58, and extracts one or more cardiac features from the raw signal. In some examples, feature delineation circuitry 260 identifies one or more cardiac features, such as one or more of RR intervals present in the cardiac electrogram data, a mean heartrate present in the cardiac electrogram data, a minimum heartrate present in the cardiac electrogram data, a maximum heartrate present in the cardiac electrogram data, a PR interval present in the cardiac electrogram data, a variability of heartrate present in the cardiac electrogram data, one or more amplitudes of one or more features of an ECG, an interval between the or more features of the ECG, a T-wave alternans, QRS morphology measures, or other types of cardiac features not expressly described herein.

As one example, feature delineation circuitry 260 identifies one or more features of a T-wave of an electrocardiogram of patient 4 to detect an episode of cardiac arrhythmia in patient 4. In some examples, the one or more identified features are one or more amplitudes of the T-wave. In some examples, the one or more identified features are a frequency of the T-wave. In some examples, the one or more identified features include at least an amplitude of the T-wave and a frequency of the T-wave. In some examples, feature delineation circuitry 260 identifies one or more relative changes in the one or more identified features that are indicative of an episode of cardiac arrhythmia in patient 4. In some examples, feature delineation circuitry 260 identifies one or more interactions between multiple identified features that are indicative of an episode of cardiac arrhythmia in patient 4. In some examples, feature delineation circuitry 260 analyzes patient data that represents one or more values that are averaged over a short-term period of time (e.g., about 3 minutes). For example, the cardiac electrogram data may include one or more of an average frequency or an average amplitude of a T-wave or a QRS wave of an electrocardiogram of patient 4 to detect the episode of cardiac arrhythmia.

Processing circuitry 50 may apply feature delineation via feature delineation circuitry 260 to determine that the one or more cardiac features are indicative of an episode of cardiac arrhythmia. In some examples, processing circuitry 50 applies feature delineation via feature delineation circuitry 260 to classify the detected episode of cardiac arrhythmia as an episode of cardiac arrhythmia of a particular type (e.g., bradycardia, tachycardia, atrial fibrillation, or ventricular fibrillation). In some examples, processing circuitry 50 performs feature delineation of the sensed cardiac electrogram data via feature delineation circuitry 260 as described in more detail below. In some examples, the feature delineation performed by IMD 10 is of a reduced complexity so as to conserve power in IMD 10. This may enable feature delineation circuitry 260 to perform initial or preliminary detection of cardiac arrhythmia.

Additionally, as described in detail below, processing circuitry 50 applies machine learning system 250 to the cardiac electrogram data to verify or classify the detection of episodes of arrhythmia by feature delineation circuitry 260. While machine learning system 250 may perform a more comprehensive and detailed analysis of the cardiac electrogram data so as to more accurately detect cardiac arrhythmia over feature delineation circuitry 260, machine learning system 250 may require more computational resources and power over feature delineation circuitry 260. By using machine learning system 250 to verify or classify the detection of episodes of arrhythmia by feature delineation circuitry 260, IMD 10 may take advantage of the high accuracy offered by machine learning system 250 while minimizing the power consumption or battery longevity of IMD 10. In some examples, processing circuitry 50 transmits, via communication circuitry 54, one or more of the cardiac electrogram data, the one or more cardiac features present in the cardiac electrogram data, an indication of an episode of cardiac arrhythmia verified by machine learning system 250, or an indication of a classification of the detected episode of cardiac arrhythmia as determined by machine learning system 250, to external device 12.

In some examples, the machine learning model implemented by machine learning system 250 is trained with training data that comprises cardiac electrogram data for a plurality of patients labeled with descriptive metadata. For example, during a training phase, machine learning system 250 processes a plurality of ECG waveforms. Typically, the plurality of ECG waveforms are from a plurality of different patients. Each ECG waveform is labeled with one or more episodes of arrhythmia of one or more types. For example, a training ECG waveform may include a plurality of segments, each segment labeled with a descriptor that specifies an absence of arrhythmia or a presence of an arrhythmia of a particular classification (e.g., bradycardia, tachycardia, atrial fibrillation, or ventricular fibrillation). In some examples, a clinician labels the presence of arrhythmia in each ECG waveform by hand. In some examples, the presence of arrhythmia in each ECG waveform is labeled according to classification by a feature delineation algorithm. Machine learning system 250 may operate to convert the training data into vectors and tensors (e.g., multi-dimensional arrays) upon which machine learning system 250 may apply mathematical operations, such as linear algebraic, nonlinear, or alternative computation operations. Machine learning system 250 uses the training data 104 to teach the machine learning model to weigh different features depicted in the cardiac electrogram data. In some examples, machine learning system 250 uses the cardiac electrogram data to teach the machine learning model to apply different coefficients that represent one or more features in a cardiac electrogram as having more or less importance with respect to an occurrence of a cardiac arrhythmia of a particular classification. By processing numerous such ECG waveforms labeled with episodes of arrhythmia, machine learning system 250 may build and train a machine learning model to receive cardiac electrogram data from a patient, such as patient 4 of FIG. 1, that machine learning system 250 has not previously analyzed, and process such cardiac electrogram data to detect the presence or absence of arrhythmia of different classifications in the patient with a high degree of accuracy. Typically, the greater the amount of cardiac electrogram data on which machine learning system 250 is trained, the higher the accuracy of the machine learning model in detecting or classifying cardiac arrhythmia in new cardiac electrogram data.

After machine learning system 250 has trained the machine learning model, machine learning system 250 may receive patient data, such as cardiac electrogram data, for a particular patient, such as patient 4. Machine learning system 250 applies the trained machine learning model to the patient data to detect an episode of cardiac arrhythmia in patient 4. Further, machine learning system 250 applies the trained machine learning model to the patient data to classify the episode of cardiac arrhythmia in patient as indicative of a particular type of arrhythmia. In some examples, machine learning system 250 may output a preliminary determination that the episode of cardiac arrhythmia is indicative of a particular type of arrhythmia, as well as an estimate of certainty in the determination. In response to determining that the estimate of certainty in the determination is greater than a predetermined threshold (e.g., 50%, 75%, 90%, 95%, 99%), processing circuitry 50 may classify that the episode of cardiac arrhythmia as the particular type of arrhythmia. As described herein, processing circuitry 50 uses machine learning system 250 to verify that feature delineation circuitry 260 has correctly detected an episode of arrhythmia or that feature delineation circuitry 260 has correctly classified an episode of arrhythmia as being of a particular type.

In some examples, machine learning system may process one or more cardiac features of cardiac electrogram data instead of the raw cardiac electrogram data itself. The one or more cardiac features may be obtained via feature delineation performed by IMD 10, as described above. The cardiac features may include, e.g., one or more of RR intervals present in the cardiac electrogram data, a mean heartrate present in the cardiac electrogram data, a minimum heartrate present in the cardiac electrogram data, a maximum heartrate present in the cardiac electrogram data, a PR interval present in the cardiac electrogram data, a variability of heartrate present in the cardiac electrogram data, one or more amplitudes of one or more features of an ECG, a T-wave alternans, QRS morphology measures, or other types of cardiac features not expressly described herein. In such example implementations, machine learning system may train the machine learning model via a plurality of training cardiac features labeled with episodes of arrhythmia, instead of the plurality of ECG waveforms labeled with episodes of arrhythmia as described above.

In some examples, machine learning system 250 may apply the machine learning model to other types of data to determine that an episode of arrhythmia has occurred in patient 4. For example, machine learning system 250 may apply the machine learning model to one or more characteristics of cardiac electrogram data that are correlated to arrhythmia in the patient, an activity level of IMD 10, an input impedance of IMD 10, or a battery level of IMD 10.

In further examples, processing circuitry 50 may generate, from the cardiac electrogram data, an intermediate representation of the cardiac electrogram data. For example, processing circuitry 50 may apply one or more signal processing, signal decomposition, wavelet decomposition, filtering, or noise reduction operations to the cardiac electrogram data to generate the intermediate representation of the cardiac electrogram data. In this example, machine learning system 250 processes such an intermediate representation of the cardiac electrogram data to detect and classify an episode of arrhythmia in patient 4. Furthermore, machine learning system 250 may train the machine learning model via a plurality of training intermediate representations labeled with episodes of arrhythmia, instead of the plurality of raw ECG waveforms labeled with episodes of arrhythmia as described above. The use of such intermediate representations of the cardiac electrogram data may allow for the training and development of a lighter-weight, less computationally complex machine learning model by machine learning system 250. Further, the use of such intermediate representations of the cardiac electrogram data may require less iterations and fewer training data to build an accurate machine learning model, as opposed to the use of raw cardiac electrogram data to train the machine learning model.

In some examples, memory 56 includes arrhythmia dictionary 270. In some examples, arrhythmia dictionary 270 includes a plurality of entries. Each entry of the plurality of entries includes a classification of cardiac arrhythmia of one or more particular types (e.g., bradycardia, tachycardia, atrial fibrillation, or ventricular fibrillation). Further, the entry includes one or more cardiac features indicative of the classification of cardiac arrhythmia. As described in more detail below, processing circuitry 50 uses arrhythmia dictionary 270 to classify an episode of arrhythmia detected via feature delineation circuitry 260 as being a particular type of arrhythmia. Further, processing circuitry 50 applies machine learning system 250 to classify detected episodes of arrhythmia for which arrhythmia dictionary 270 does not contain a corresponding entry so as to build robust entries for arrhythmia dictionary 270.

Although described herein in the context of example IMD 10 that senses cardiac electrogram data of patient 4, the techniques for cardiac arrhythmia detection disclosed herein may be used with other types of devices. For example, the techniques may be implemented with an extra-cardiac defibrillator coupled to electrodes outside of the cardiovascular system, a transcatheter pacemaker configured for implantation within the heart, such as the Micra™ transcatheter pacing system commercially available from Medtronic PLC of Dublin Ireland, an insertable cardiac monitor, such as the Reveal LINQ™ ICM, also commercially available from Medtronic PLC, a SEEQ™ Mobile Cardiac Telemetry (MCT) device available from Medtronic plc, of Dublin, Ireland, a neurostimulator, a drug delivery device, a medical device external to patient 4, a wearable device such as a wearable cardioverter defibrillator, a fitness tracker, or other wearable device, a mobile device, such as a mobile phone, a "smart" phone, a laptop, a tablet computer, a personal digital assistant (PDA), or "smart" apparel such as "smart" glasses, a "smart" patch, or a "smart" watch.

Figure 3:
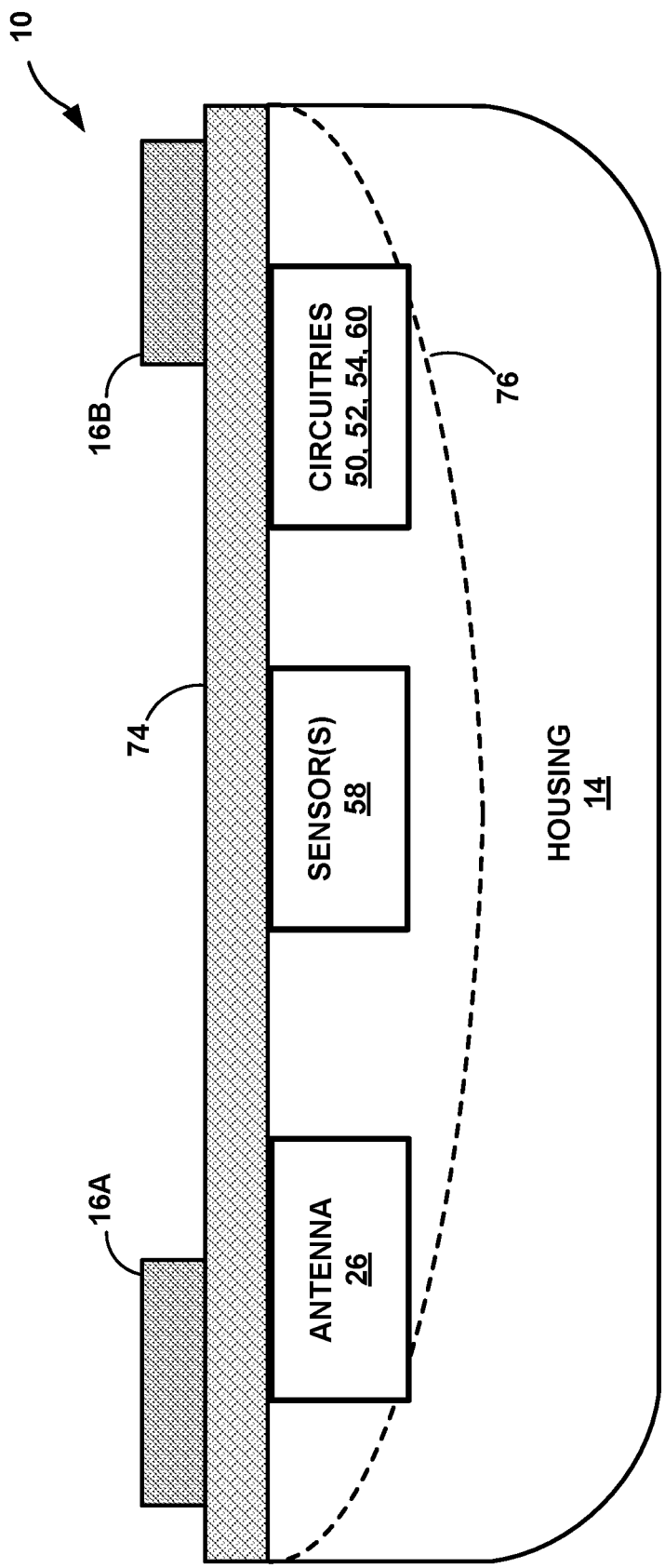
FIG. 3 is a block diagram illustrating an example configuration of the implantable medical device of FIG. 1.

FIG. 3 is a block diagram illustrating an example configuration of implantable medical device of FIG. 1. The components of FIG. 3 may not necessarily be drawn to scale, but instead may be enlarged to show detail. Specifically, FIG. 3 is a block diagram of a top view of an example configuration of an IMD 10 of FIG. 1.

FIG. 3 is a conceptual drawing illustrating an example IMD 10 that may include components substantially similar to IMD 10 of FIG. 1. In addition to the components illustrated in FIGS. 1 and 2, the example of IMD 10 illustrated in FIG. 3 also may include a wafer-scale insulative cover 74, which may help insulate electrical signals passing between electrodes 16A, 16B on housing 14 and processing circuitry 50. In some examples, insulative cover 74 may be positioned over an open housing 14 to form the housing for the components of IMD 10B. One or more components of IMD 10B (e.g., antenna 26, processing circuitry 50, sensing circuitry 52, communication circuitry 54, and/or switching circuitry 60) may be formed on a bottom side of insulative cover 74, such as by using flip-chip technology. Insulative cover 74 may be flipped onto housing 14. When flipped and placed onto housing 14, the components of IMD 10 formed on the bottom side of insulative cover 74 may be positioned in a gap 78 defined by housing 14. Housing 14 may be formed from titanium or any other suitable material (e.g., a biocompatible material), and may have a thickness of about 200 micrometers to about 500 micrometers. These materials and dimensions are examples only, and other materials and other thicknesses are possible for devices of this disclosure.

In some examples, IMD 10 collects, via sensing circuitry 50 and/or sensors 58, patient data of patient 4 including cardiac electrogram data. Sensors 58 may include one or more sensors, such as one or more accelerometers, pressure sensors, optical sensors for 02 saturation, etc. In some examples, the patient data includes one or more of an activity level of the patient, a heartrate of the patient, a posture of the patient, a cardiac electrogram of the patient, a blood pressure of the patient, accelerometer data for the patient, or other types of patient parametric data. In some examples, IMD 10 uploads, via communication circuitry 54, the patient data to external device 12, which may in turn upload such data to a remote monitoring center or patient monitoring network. In some examples, IMD 10 uploads the patient data on a daily basis. In some examples, the patient data includes one or more values that represent average measurements of patient 4 over a long-term time period (e.g., about 24 hours to about 48 hours). In this example, IMD 10 both uploads the patient data and performs arrhythmia detection and classification of patient 4 (as described below). However, in other examples, the medical device that processes the patient data to detect and/or classify arrhythmia in patient 4 is different from the medical device that performs short-term monitoring of patient 4. For example, IMD 10 may perform short-term monitoring of patient 4 and external device 12 processes the patient data to detect and/or classify arrhythmia in patient 4.

Figure 4:
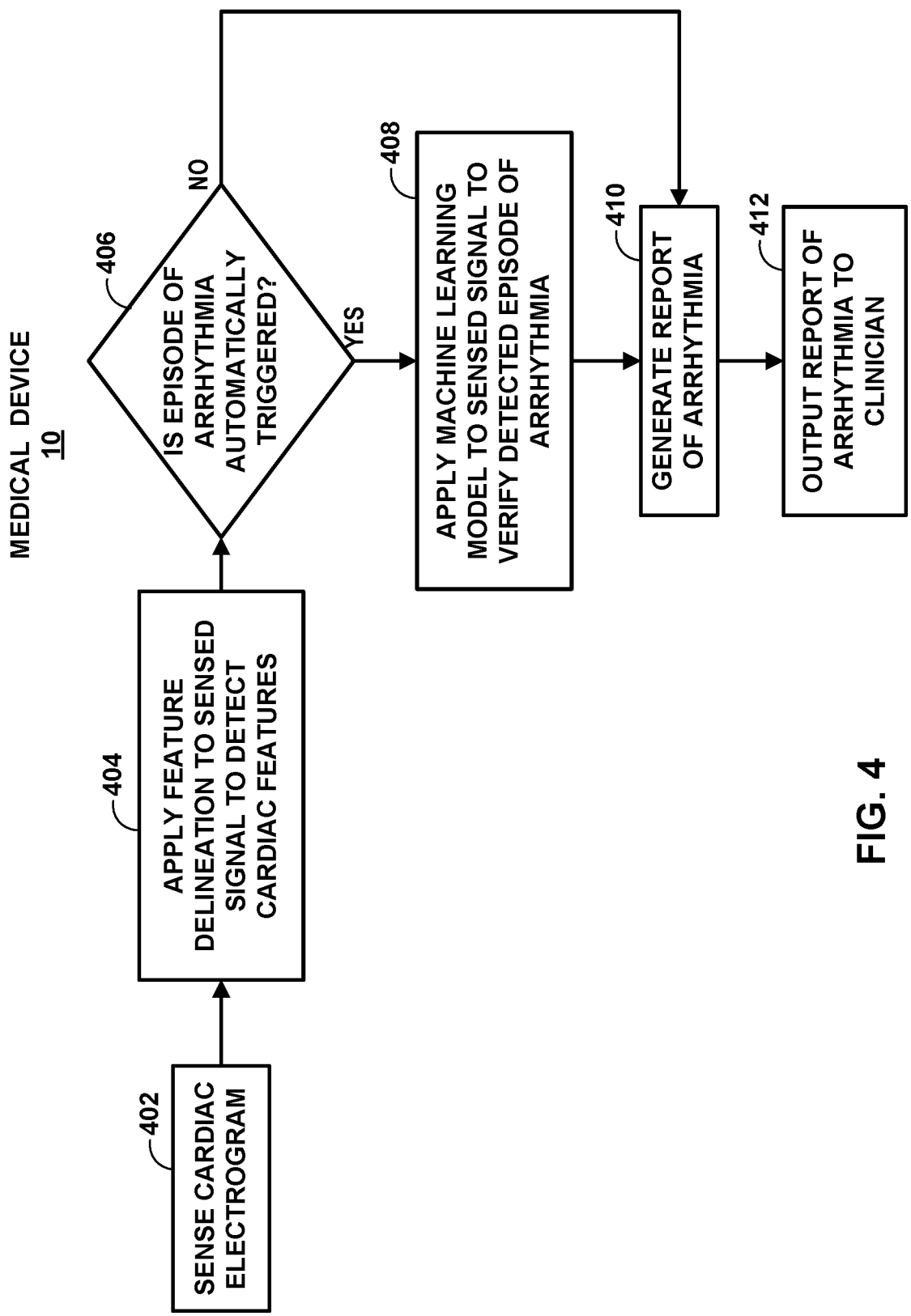
FIG. 4 is a flowchart illustrating an example operation in accordance with the techniques of the disclosure.

FIG. 4 is a flowchart illustrating an example operation in accordance with the techniques of the disclosure. For convenience, FIG. 4 is described with respect to FIG. 1. In some examples, the operation of FIG. 4 is an operation for detecting and classifying cardiac arrhythmia in patient 4. In the operation of FIG. 4, system 2 combines the accuracy of the machine learning model of machine learning system 250 in detecting cardiac arrhythmia with the low power consumption of feature delineation algorithms. While the operation of FIG. 4 is described with respect to IMD 10 of FIG. 1, in other examples, the operation of FIG. 4 may be performed by, e.g., external device 12 or a combination of IMD 10 and external device 12.

As depicted in FIG. 4, IMD 10 senses cardiac electrogram data of patient 4 (402). The cardiac electrogram data can be, e.g., an episodic ECG of patient 4 or a full-disclosure ECG of patient 4. Further, the cardiac electrogram data of patient 4 may be from a single-channel or multi-channel system. For simplicity, in the example of FIG. 4, the cardiac electrogram data of patient 4 is described as single-channel episodic ECG data.

IMD 10 applies feature delineation to the cardiac electrogram data to detect one or more cardiac features (404). IMD 10 further applies feature delineation to the cardiac electrogram data to detect one or more episodes of arrhythmia. For example, IMD 10 may apply QRS detection delineation and noise flagging to the cardiac electrogram data to provide arrhythmia characteristics and/or cardiac features for detected episodes of arrhythmia (e.g., a heartrate variability during an episode of atrial fibrillation, a duration of a pause). In some examples, the feature delineation is a one-size-fits-all type algorithm. In other examples, the feature delineation may be an algorithm with parameters programmed by a clinician or specific to patient 4. In some examples, IMD 10 applies feature delineation to the cardiac electrogram data to classify a detected episode of arrhythmia as a particular type of arrhythmia.

IMD 10 further determines a trigger for the detected episode of cardiac arrhythmia. For example, the episode of cardiac arrhythmia may be detected in response to an automatic trigger, in response to a baseline trigger, or in response to input received from patient 4. For example, a baseline trigger may not occur in response to a detected arrhythmia, but in response to an cardiac electrogram segment capture operation that occurs periodically (e.g., a segment that is captured upon implantation or adherence of IMD 10, or segments that are captured once every 24 hours, etc.). In some examples, IMD 10 may apply machine learning system 250 to verify only episodes of arrhythmia detected in response to an automatic trigger, while episodes of arrhythmia detected in response to baseline triggers or patient input may be reported without verification by machine learning system 250. For example, in response to determining that an episode of arrhythmia was not detected by an automatic trigger (e.g., "NO" block of 406), then IMD 10 generates a report of the arrhythmia (410) and outputs the report to a clinician or monitoring center for review (412) as described below.

In some examples, IMD 10 may use machine learning system 250 to perform several tasks. For example, IMD 10 may use machine learning system 250 to verify that the detection of cardiac arrhythmia by feature delineation was appropriate. The use of machine learning system 250 in this manner may limit the computational complexity of the machine learning model and may provide diagnostically relevant information to a clinician. For example, the machine learning model may be used with a high arrhythmia detection sensitivity to verify that an atrial fibrillation autotrigger correlates to an episode of atrial fibrillation in patient 4. As another example, the machine learning model may be used to ensure that only the portions of the cardiac electrogram that coincide with the duration of a verified episode of atrial fibrillation in patient 4 are used to compute an atrial fibrillation burden on patient 4. As described herein, the burden of an episode of arrhythmia is a ratio of a length of time of the episode of arrhythmia to a length of time during of monitoring of the patient by IMD 10.

As another example, IMD 10 may use machine learning system 250 to detect the presence of other episodes of arrhythmia not detected by feature delineation but that coincide with the episode of arrhythmia detected by feature delineation. For example, IMD 10 may use machine learning system 250 to detect a presence of "high-importance" arrhythmias, such as pause, atrial fibrillation, or ventricular tachycardia. The use of a machine learning model that is designed to detect a presence or absence of an episode of cardiac arrhythmia of a set of types of arrhythmias may be more limited in computational complexity than a machine learning model that is designed to detect the exact type and instance of occurrence of an episode of cardiac arrhythmia.

For example, with respect to the operation of FIG. 4, in response to determining that the episode of cardiac arrhythmia is detected in response to an automatic trigger, (e.g., "YES" block of 406), IMD 10 applies a machine learning model of machine learning system 250 to the cardiac electrogram data to verify the detection of the episode of cardiac arrhythmia by the feature delineation (408). In some examples, IMD 10 applies the machine learning model of machine learning system 250 to the cardiac electrogram data to verify a classification of the episode of cardiac arrhythmia by the feature delineation.

In some examples, an episode of arrhythmia detected in response to an automatic trigger is of a same limited duration (e.g., 30 seconds before and after arrhythmia detection) and typically shorter in duration than patient triggered episodes. In some examples, the machine learning model receives, as an input, at least a portion of a cardiac electrogram waveform that caused the automatic trigger and a reason for trigger (e.g., detection via feature delineation of an atrial fibrillation, a bradycardia, or a pause). The cardiac electrogram waveform may be, e.g., an ECG waveform.

In some examples, the machine learning model receives, as an input, a pre-processed version of the cardiac electrogram waveform, or a signal decomposition of the cardiac electrogram waveform. For example, IMD 10 may apply preprocessing to the cardiac electrogram waveform by applying a down-sampling or signal normalization operation to the waveform so as to generate an intermediate representation of the cardiac electrogram. Signal decomposition is the use of wavelet decomposition bands or a frequency domain representation (e.g., spectrogram). In some examples, IMD 10 may apply preprocessing to the cardiac electrogram waveform to reduce the computational complexity of the machine learning model. For example, by down-sampling a record originally sampled at 200 samples per second to 100 samples per second, IMD 10 may require half the computational resources to process the down-sampled record as the original record. Similarly, by using the same signal decomposition as that used for arrhythmia detection, IMD 10 may leverage pre-computed data to reduce computational complexity of machine learning system 250 because the machine learning model does not have to learn an optimal set of signal convolution layers.

In response to verifying that the detection of the episode of cardiac arrhythmia by the feature delineation is correct, IMD 10 stores and/or transmits cardiac electrogram data for the episodes to a monitoring center or a clinician for review. For example, IMD 10 generates a report of the arrhythmia (410) and outputs the report to a clinician or monitoring center (412). Typically, only those episodes of cardiac arrhythmia detected by feature delineation that are verified as appropriate or important by machine learning system 250 are stored and transmitted for monitoring center and/or clinician review. For example, if machine learning system 250 detects an episode of bradycardia and feature delineation performed on the cardiac electrogram data indicates that 4 out of 4 non-noisy heartbeats are less than 30 beats-per-minute (BPM), then IMD 10 generates a report notifying the physician of the occurrence of the episode of arrhythmia.

In one example, the report includes an indication that the episode of arrhythmia has occurred in the patient and one or more of the cardiac features that coincide with the episode of arrhythmia. In some examples, the report further includes a classification of the episode of arrhythmia as a particular type of arrhythmia. In some examples, the report includes a subsection of the cardiac electrogram data obtained from patient 4 that coincides with the episode of arrhythmia. For example, IMD 10 may identify a subsection of the cardiac electrogram data of patient 4, wherein the subsection comprises cardiac electrogram data for a first time period prior to the episode of arrhythmia (e.g., typically less than 10 minutes prior to the onset of the episode of arrhythmia), a second time period during the occurrence of the episode of arrhythmia, and a third time period after the episode of arrhythmia (e.g., typically less than 10 minutes after the cessation of the episode of arrhythmia). In some examples, the episode duration differs by device type, and may further depend on a use case for the medical device, one or more settings of the medical device, or a particular type of arrhythmia sensed. For example, some types of arrhythmia self-terminate quickly, (resulting in a short duration episode), while other types of arrhythmia are sustained and of a length such that the recorded duration of the episode may depend on a designated memory space on the medical device. Typically, a length of time of the cardiac electrogram data of the patient is greater than the first, second, and third time periods. Further, IMD 10 identifies one or more of the cardiac features that coincide with the first, second, and third time periods. IMD 10 includes, in the report, the subsection of the cardiac electrogram data and the one or more of the cardiac features that coincide with the first, second, and third time periods.

In some examples, IMD 10 receives, in response to the report, one or more adjustments to one or more parameters used by IMD 10 to sense the cardiac electrogram data of patient 4. IMD 10 perform such adjustments to for subsequent sensing of the cardiac electrogram data of patient 4.

Figure 5:
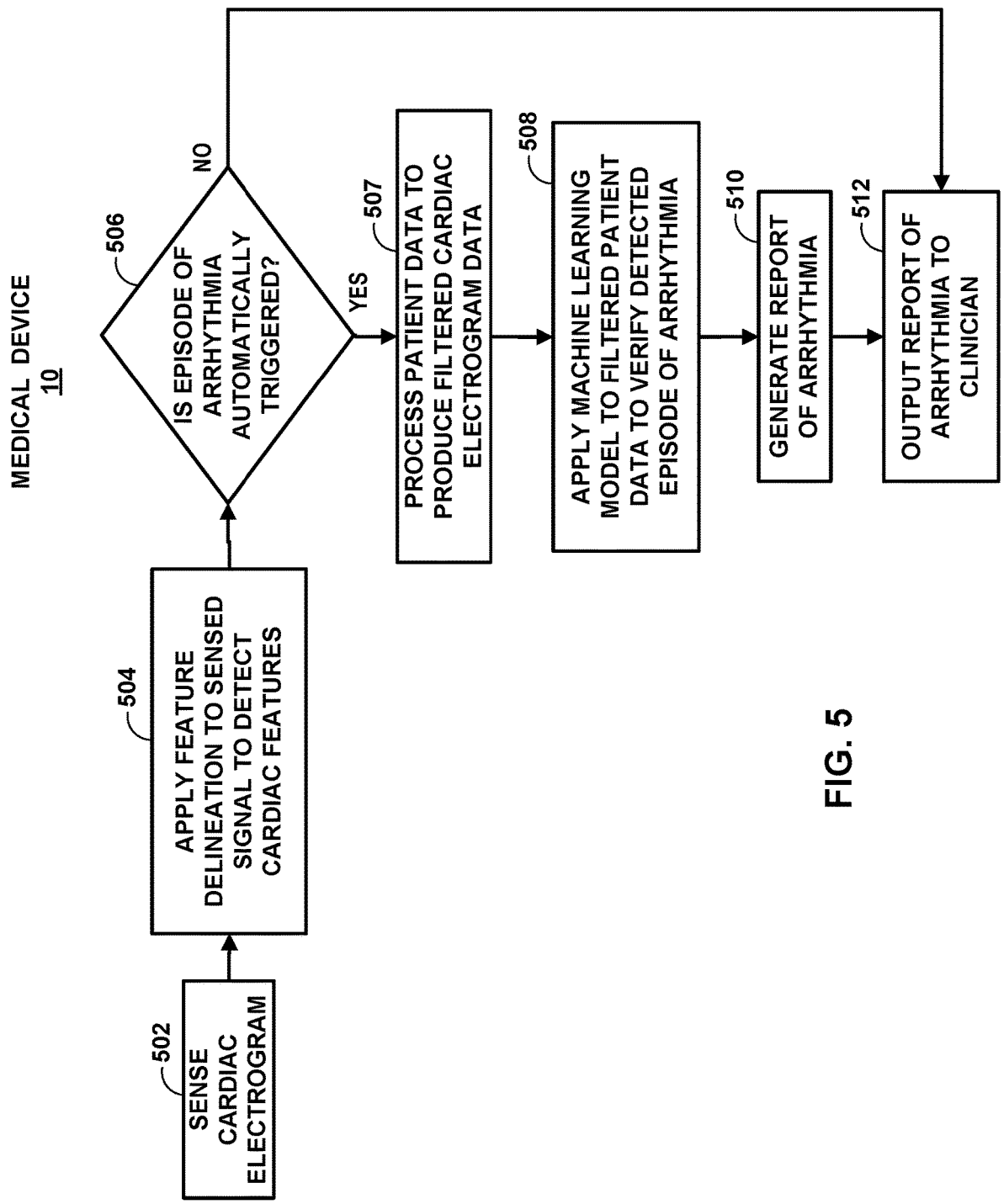
FIG. 5 is a flowchart illustrating an example operation in accordance with the techniques of the disclosure.

FIG. 5 is a flowchart illustrating an example operation in accordance with the techniques of the disclosure. For convenience, FIG. 5 is described with respect to FIG. 1. In some examples, the operation of FIG. 5 is an operation for detecting and classifying cardiac arrhythmia in patient 4. In the operation of FIG. 5, system 2 combines the accuracy of the machine learning model of machine learning system 250 in detecting cardiac arrhythmia with the low power consumption of feature delineation algorithms. While the operation of FIG. 5 is described with respect to IMD 10 of FIG. 1, in other examples, the operation of FIG. 5 may be performed by, e.g., external device 12 or a combination of IMD 10 and external device 12.

As depicted in FIG. 5, IMD 10 senses cardiac electrogram data of patient 4 (502). IMD 10 applies feature delineation to the cardiac electrogram data to detect one or more cardiac features (504). IMD 10 further determines whether the episode of cardiac arrhythmia was detected in response to an automatic trigger (506). For example, in response to determining that an episode of arrhythmia was not detected by an automatic trigger (e.g., "NO" block of 506), such as may be the case for an episode of cardiac arrhythmia detected in response to a baseline trigger, or in response to input received from patient 4, then IMD 10 generates a report of the arrhythmia (510) and outputs the report to a clinician or monitoring center for review (512). The operation of steps 502, 504, 506, 510, and 512 may occur in a substantially similar fashion to steps 402, 404, 406, 410, and 412 of FIG. 4, respectively.

In response to determining that the episode of cardiac arrhythmia is detected in response to an automatic trigger, (e.g., "YES" block of 506), then IMD processes the cardiac electrogram data to produce filtered cardiac electrogram data (507). For example, IMD 10 may condition cardiac electrogram data, such as one or more ECG episodes, based on device and physiological parameters such as the input impedance, activity level and posture changes to produce the filtered cardiac electrogram data. For example, during periods of time wherein patient 4 is exhibiting high activity levels or during periods of time wherein IMD 10 is undergoing highly-varying levels of input impedance, feature delineation may falsely detect episodes of cardiac arrhythmia due to automatic triggers in response to noise in the cardiac electrogram data. The use of filtered cardiac electrogram data may allow IMD 10 to discard these periods of noisy data which may be subject to signal artifacts such as amplitude level changes. Furthermore, the use of filtered cardiac electrogram data may reduce the computational complexity of the machine learning model because the machine learning model may be designed to analyze non-noisy data. Additionally, the use of filtered cardiac electrogram data may allow IMD 10 to avoid using the machine learning model to verify that an episode of arrhythmia was correctly detected by feature delineation where the episode of arrhythmia is likely to be falsely triggered due to noise in the cardiac electrogram data, further reducing the power consumption by IMD 10. In some examples, automatically triggered episodes of cardiac arrhythmia that are associated with pause-related syncope or bradycardia may not be suppressed from processing by the machine learning model.

IMD 10 applies a machine learning model of machine learning system 250 to the filtered cardiac electrogram data to verify the detection of the episode of cardiac arrhythmia by the feature delineation (508). In some examples, IMD 10 applies the machine learning model of machine learning system 250 to the filtered cardiac electrogram data to verify a classification of the episode of cardiac arrhythmia by the feature delineation. In response to verifying that the detection of the episode of cardiac arrhythmia by the feature delineation is correct, IMD 10 stores and/or transmits cardiac electrogram data for the episodes to a monitoring center or a clinician for review. For example, IMD 10 generates a report of the arrhythmia (510) and outputs the report to a clinician or monitoring center (512) as described above.

Figure 6:
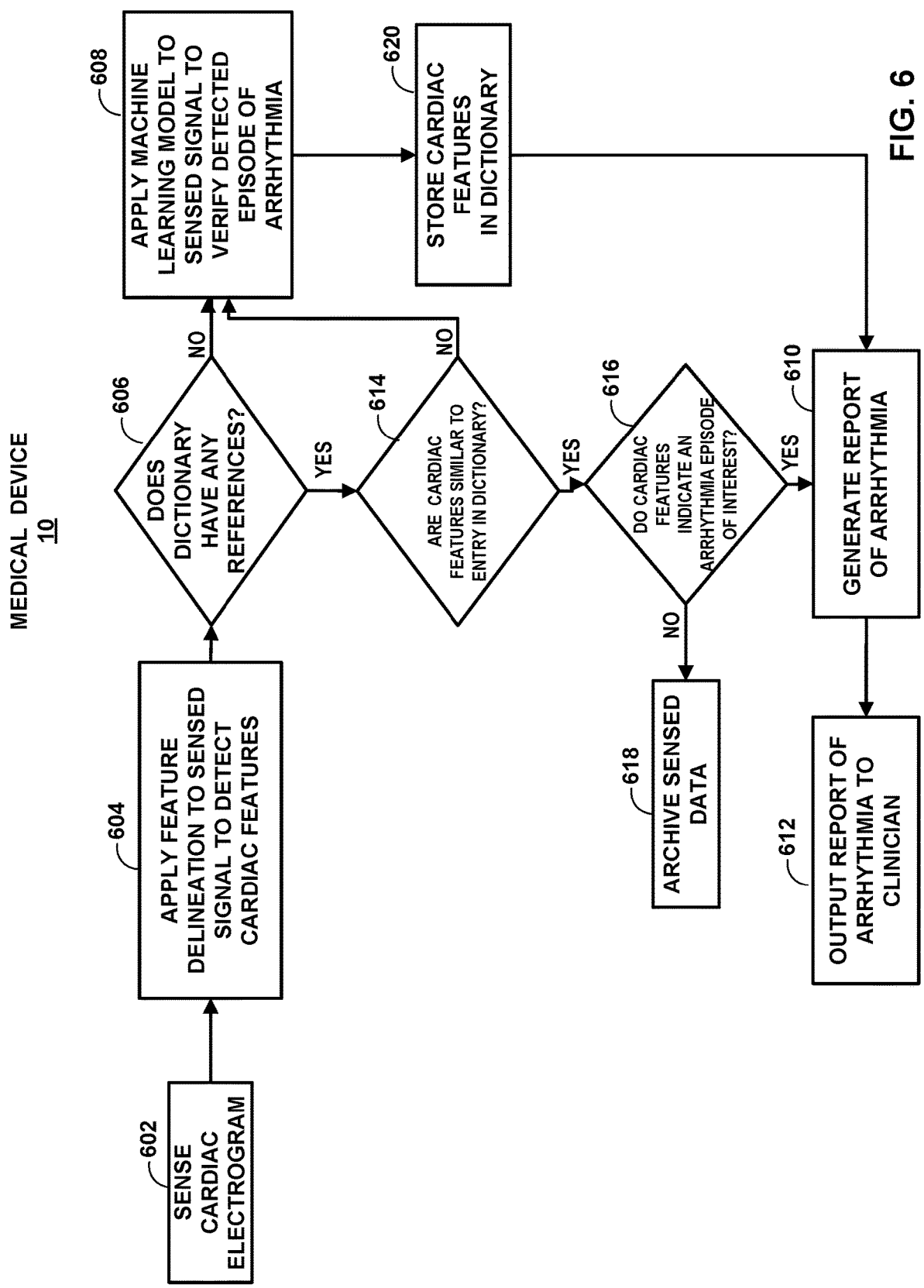
FIG. 6 is a flowchart illustrating an example operation in accordance with the techniques of the disclosure.

FIG. 6 is a flowchart illustrating an example operation in accordance with the techniques of the disclosure. For convenience, FIG. 6 is described with respect to FIGS. 1 and 2. In some examples, the operation of FIG. 6 is an operation for detecting and classifying cardiac arrhythmia in patient 4 using an arrhythmia dictionary built by machine learning system 250. In the operation of FIG. 6, system 2 combines the accuracy of the machine learning model of machine learning system 250 in detecting cardiac arrhythmia with the low power consumption of feature delineation algorithms. While the operation of FIG. 6 is described with respect to IMD 10 of FIG. 1, in other examples, the operation of FIG. 6 may be performed by, e.g., external device 12 or a combination of IMD 10 and external device 12.

As depicted in FIG. 6, IMD 10 senses cardiac electrogram data of patient 4 (602). IMD 10 applies feature delineation to the cardiac electrogram data to detect one or more cardiac features (604). The operation of steps 602 and 604 may occur in a substantially similar fashion to steps 402 and 404 of FIG. 4, respectively.

IMD 10 determines whether arrhythmia dictionary 270 includes at least one entry (606). Each entry of arrhythmia dictionary 270 includes a classification defining an episode of arrhythmia as a specific type of arrhythmia or set of arrhythmias, such as an episode of bradycardia, tachycardia, atrial fibrillation, ventricular fibrillation, or AV Block. Each entry further includes one or more cardiac features associated with an episode of cardiac arrhythmia of the corresponding classification. In response to determining that arrhythmia dictionary 270 includes at least one entry (e.g., "YES" block of 606), IMD 10 determines whether the cardiac features obtained via feature delineation are similar to cardiac features of the entry in arrhythmia dictionary 270 (614). For example, IMD 10 may compare one or more parameters of the cardiac features obtained via feature delineation to one or more parameters of the cardiac features of the entry in the arrhythmia dictionary. In some examples, IMD 10 may determine the similarity between the cardiac features obtained via feature delineation and the cardiac features of the entry in arrhythmia dictionary 270 by applying computationally efficient methods such as L1 distance, percent similarity, or if-then-else rules.

For example, IMD 10 determines a similarity of an L1 distance of the cardiac features obtained via feature delineation to an L1 distance of the cardiac features of each entry of the plurality of entries of arrhythmia dictionary. In another example, IMD 10 determines whether a difference between at least one parameter of the cardiac features obtained via feature delineation and at least one parameter of the cardiac features of each entry of the plurality of entries of arrhythmia dictionary 270 is greater than a predetermined threshold.

In response to determining that the cardiac features obtained via feature delineation are similar to cardiac features of the entry in the arrhythmia dictionary (e.g., "YES" block of 614), IMD 10 determines whether the entry in the arrhythmia dictionary defines the cardiac features as indicative of an episode of arrhythmia of interest (616). In response to determining that the entry in the arrhythmia dictionary defines the cardiac features as indicative of an episode of arrhythmia of interest (e.g., "YES" block of 616), IMD 10 generates a report of the arrhythmia (610) and outputs the report to a clinician or monitoring center for review (612). The operation of steps 610 and 612 may occur in a substantially similar fashion to steps 410 and 412 of FIG. 4, respectively.

In response to determining that the entry in the arrhythmia dictionary defines the cardiac features as not indicative of an episode of arrhythmia of interest (e.g., "NO" block of 616), IMD 10 may archive the sensed cardiac electrogram data for review by a monitoring center or clinician at a later time (618). For example, if the episode of arrhythmia is an episode of normal sinus rhythm (NSR), Premature ventricular contractions (PVCs), Premature atrial contractions (PACs), or one or more signal artifacts due to noise, then IMD 10 stores the characteristics of the detected episode (e.g., mean, median RR, RR variation, average QRS morphology, QRS morphology deviation), for reference at a later time. In some examples, the cardiac electrogram data for the episode is not used for further processing or reporting.

In response to determining that arrhythmia dictionary 270 does not include at least one entry (e.g., "NO" block of 606), or in response to determining that the cardiac features obtained via feature delineation are not similar to any entry in arrhythmia dictionary 270 (e.g., "NO" block of 614), then IMD 10 applies a machine learning model of machine learning system 250 to the cardiac electrogram data to verify the detection of the episode of cardiac arrhythmia by the feature delineation (608) and/or detect any other arrhythmias of interest. The operation of step 608 may occur in a substantially similar fashion to step 408 of FIG. 4. In response to verifying that the detection of the episode of cardiac arrhythmia by the feature delineation is correct or that other arrhythmias of interest are present, IMD 10 stores the cardiac features in arrhythmia dictionary 270 (620). For example, IMD 10 creates a new entry in arrhythmia dictionary 270 that defines a classification of the episode of arrhythmia and includes the one or more cardiac features obtained via feature delineation that is indicative of the classification of the episode of arrhythmia. Thus, IMD 10 may use machine learning system 250 to build, maintain, and update arrhythmia dictionary 270 for detecting and classifying episodes of cardiac arrhythmia. Furthermore, the use of machine learning system 250 only to verify and classify a first instance of each type of arrhythmia may limit the use of machine learning system 250, thereby conserving power in IMD 10. In some examples, machine learning system 250 is used only to verify and classify episodes of cardiac arrhythmia detected in response to automatic triggers. In some examples, after storing the cardiac features as a new entry in arrhythmia dictionary 270, IMD 10 generates a report of the arrhythmia (610) and outputs the report to a clinician or monitoring center for review (612).

Figure 7:
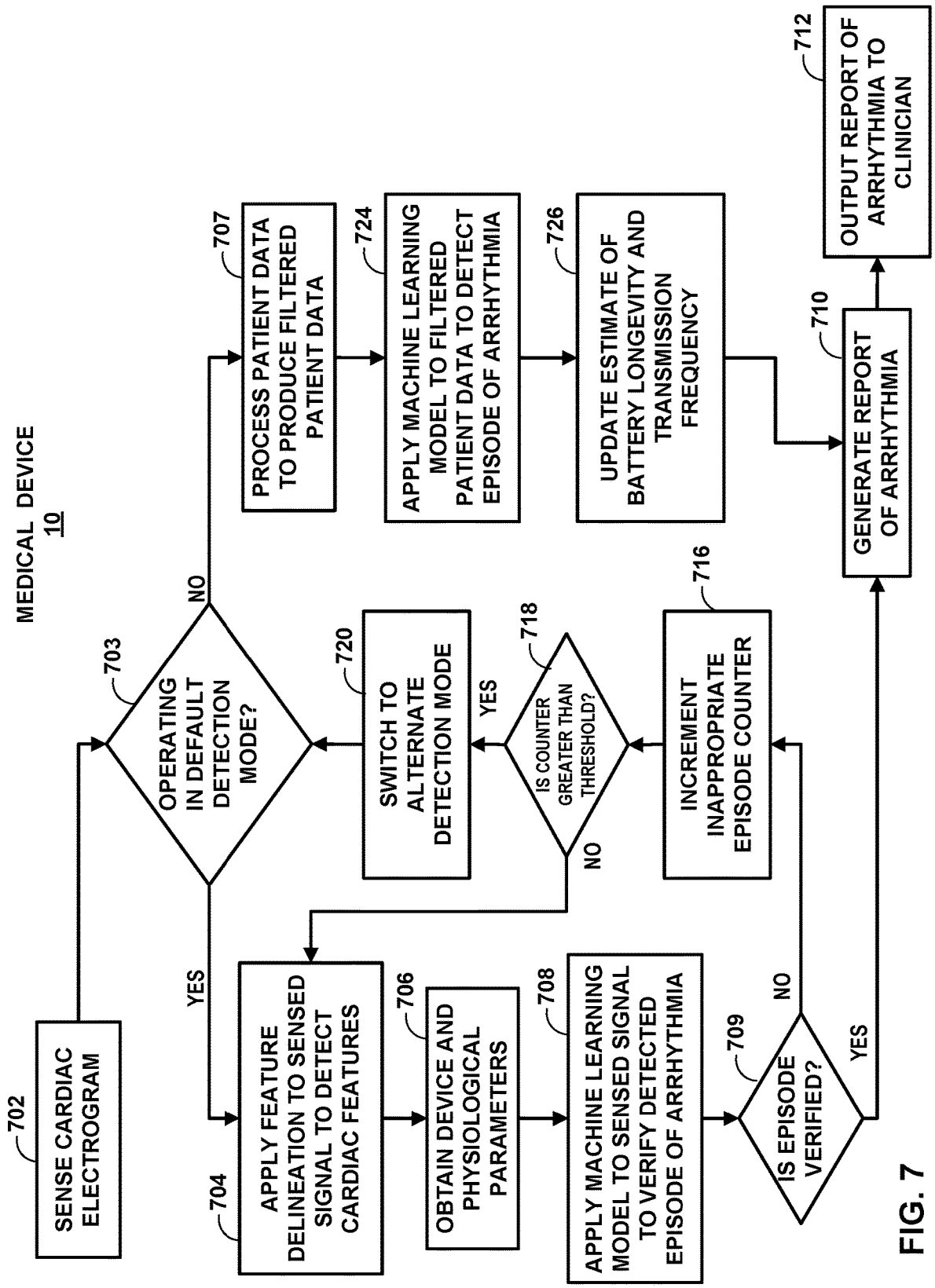
FIG. 7 is a flowchart illustrating an example operation in accordance with the techniques of the disclosure.

FIG. 7 is a flowchart illustrating an example operation in accordance with the techniques of the disclosure. For convenience, FIG. 7 is described with respect to FIG. 1. In some examples, the operation of FIG. 7 is an operation for detecting and classifying cardiac arrhythmia in patient 4. The operation of FIG. 7 may provide tradeoffs between battery life and device longevity for arrhythmia detection accuracy in patients where, e.g., the operation of FIG. 4 for detecting and classifying cardiac arrhythmia, does not appropriately trigger or detect episodes of arrhythmia in patient 4. While the operation of FIG. 7 is described with respect to IMD 10 of FIG. 1, in other examples, the operation of FIG. 7 may be performed by, e.g., external device 12 or a combination of IMD 10 and external device 12.

In most patients, (e.g., between about 80%-90%), the cardiac arrhythmia detection operations described by, e.g., FIGS. 4 and 5 provide increased accuracy in arrhythmia detection while avoiding adverse power consumption. However, in the remainder subpopulation, the operations described by, e.g., FIGS. 4 and 5 may not provide as high accuracy in arrhythmia detection due to various physiological reasons, such as the placement of IMD 10 (e.g., which may cause the morphology of the cardiac electrogram to change due to shifting or movement of IMD 10) or patient characteristics. For arrhythmia diagnosis, a patient in such a subpopulation may benefit from an arrhythmia detection scheme that is more sensitive and of higher complexity, even though such a scheme may consume more power (and cause a commensurate reduction in maximum battery life of IMD 10), as opposed to removing IMD 10 or changing IMD 10 with another device. The operation of FIG. 7 sets forth techniques for switching arrhythmia detection methods from the operation of, e.g., FIG. 4 or 5, to a higher-complexity machine learning arrhythmia detection scheme.

As depicted in FIG. 7, IMD 10 senses cardiac electrogram data of patient 4 (702). The operation of step 702 may occur in a substantially similar fashion to step 402 of FIG. 4. IMD 10 determines whether IMD 10 is operating in a default cardiac arrhythmia detection mode (e.g., such as the operation of FIG. 4 or 5) (703). Typically, IMD 10 commences operation in such a default mode. In response to determining that IMD 10 is operating in the default mode (e.g., "YES" block of 703), IMD 10 applies feature delineation to the cardiac electrogram data to detect one or more cardiac features indicative of an episode of arrhythmia (704). In some examples, IMD 10 obtains additional device and physiological parameters (706). IMD 10 applies a machine learning model of machine learning system 250 to the cardiac electrogram data to verify the detection of the episode of cardiac arrhythmia by the feature delineation (708). In some examples, IMD 10 applies the machine learning model to the cardiac electrogram data to detect one or more episodes of cardiac arrhythmia of other classifications not detected by feature delineation. In some examples, IMD 10 applies the machine learning model to the cardiac electrogram data and the device and physiological parameters to perform the verification or detection. The operation of steps 704 and 708 may occur in a substantially similar fashion to steps 404 and 408 of FIG. 4.

IMD 10 verifies, based on the machine learning model, whether feature delineation correctly detected the episode of cardiac arrhythmia (709). In response to verifying that the detection of the episode of cardiac arrhythmia by the feature delineation is correct (e.g., "YES" block of 709), IMD 10 generates a report of the arrhythmia (710) and outputs the report to a clinician or monitoring center (712). The operation of steps 704 and 708 may occur in a substantially similar fashion to steps 704 and 708 of FIG. 4. In some examples, IMD 10 may continue to operate according to the default cardiac arrhythmia detection scheme.

In response to verifying that the detection of the episode of cardiac arrhythmia by the feature delineation is not correct (e.g., "NO" block of 709), IMD 10 increments a counter of inappropriate instances of detected cardiac arrhythmia (716). In some examples, IMD 10 increments the counter when feature delineation incorrectly determines that an episode of cardiac arrhythmia has occurred in patient 4.

In some examples, IMD 10 increments the counter when feature delineation incorrectly classifies the episode of cardiac arrhythmia in patient 4 as an episode of a particular type of arrhythmia.

If, per the machine learning model, the feature delineation persistently detects episodes of cardiac arrhythmia inappropriately or episodes that contain no arrhythmia, then IMD 10 switches from the default cardiac arrhythmia detection mode to a second mode that uses a machine learning model for arrhythmia detection. For example, IMD determines whether the counter inappropriate instances of detected cardiac arrhythmia is greater than a predetermined threshold (718). If the counter is not greater than the predetermined threshold (e.g., "NO" block of 718), then IMD 10 continues operation according to the default cardiac arrhythmia detection scheme. If the counter is greater than the predetermined threshold (e.g., "YES" block of 718), IMD 10 switches to the alternate arrhythmia detection mode (720). In some examples, IMD 10 does not switch detection modes until physiological and device characteristics are met. For example, IMD 10 may postpone switching detection modes until proper device adherence, patient 4 is in a low- or mid-activity level), and no patient trigger of arrhythmia is active. In some examples, IMD 10 turns off machine learning arrhythmia detection for the duration of a patient-activated trigger that captures cardiac electrogram data.

During subsequent operation, IMD 10 senses cardiac electrogram data of patient 4 (702). In response to determining that IMD 10 is not operating in the default mode (e.g., "NO" block of 703), IMD processes the cardiac electrogram data to produce filtered cardiac electrogram data (707). The operation of step 707 may occur in a substantially similar fashion to step 507 of FIG. 5. IMD 10 applies a second machine learning model of machine learning system 250 to the filtered cardiac electrogram data to detect an episode of cardiac arrhythmia present in the filtered cardiac electrogram data (724). In some examples, the second machine learning model receives, as an input, at least a portion of a cardiac electrogram waveform, one or more device parameters, or one or more physiological parameters. The cardiac electrogram waveform may be, e.g., an ECG waveform.

Because the second machine learning model is of a higher complexity than feature delineation detection of cardiac arrhythmia, the second machine learning model may adversely affect the power consumption and battery life of IMD 10. Therefore, IMD 10 updates an estimate of battery longevity (726). In some examples, IMD 10 may adjust a frequency or periodicity of transmissions to external device 12. For example, to conserve battery life, IMD 10 may switch from uploading patient data, such as the sensed cardiac electrogram data, on a daily basis to uploading such data on a weekly basis to increase device longevity. IMD 10 generates a report of the arrhythmia (710) and outputs the report to a clinician or monitoring center (712).

Figure 8:
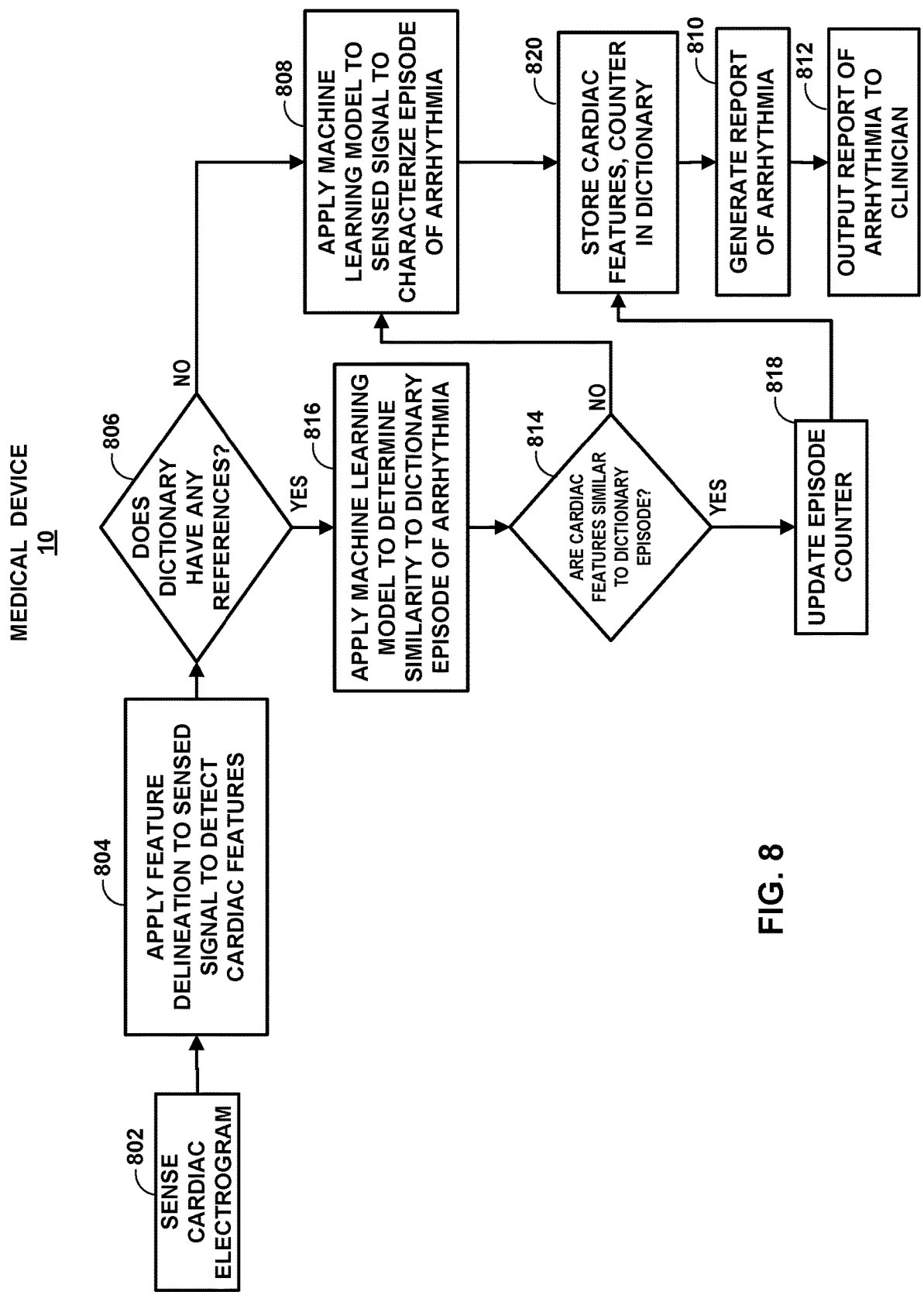
FIG. 8 is a flowchart illustrating an example operation in accordance with the techniques of the disclosure.

FIG. 8 is a flowchart illustrating an example operation in accordance with the techniques of the disclosure. For convenience, FIG. 8 is described with respect to FIGS. 1 and 2. In some examples, the operation of FIG. 8 is an operation for detecting and classifying cardiac arrhythmia in patient 4 using an arrhythmia dictionary built by machine learning system 250. In the operation of FIG. 8, system 2 combines the accuracy of the machine learning model of machine learning system 250 in detecting cardiac arrhythmia with the low power consumption of feature delineation algorithms. While the operation of FIG. 8 is described with respect to IMD 10 of FIG. 1, in other examples, the operation of FIG. 8 may be performed by, e.g., external device 12 or a combination of IMD 10 and external device 12.

In some applications, such as syncope and atrial fibrillation monitoring, the arrhythmias of interest (e.g., pause, sinus brady, atrial fibrillation), as well as the corresponding cardiac features of such arrhythmias, are known to the clinician. Thus, the techniques of the disclosure may implement appropriate algorithms on IMD 10 that use automatic triggers for arrhythmia detection. However, for other types of applications, such as post-Myocardial Infarction monitoring (e.g., where characteristics such as premature ventricular contractions (PVCs) burden, ST-segment, etc. may be of interest), or post-transcatheter aortic valve replacement (TAVR) monitoring, the exact arrhythmias or conditions of interest may not be known. Accordingly, the operation of FIG. 8 implements a generic machine learning model that can be used across multiple applications without developing specific arrhythmia detection algorithms.

The operation of FIG. 8 may be substantially similar to the operation of FIG. 6. However, as discussed in more detail below, the operation of FIG. 8 applies a machine learning system to determine whether cardiac features obtained via feature delineation are similar to cardiac features of an entry of arrhythmia dictionary 270 to determine whether the cardiac features obtained via feature delineation are indicative of an episode of arrhythmia of a classification that is the same as a classification of the entry of arrhythmia dictionary 270.

As depicted in FIG. 8, IMD 10 senses cardiac electrogram data of patient 4 (802). IMD 10 applies feature delineation to the cardiac electrogram data to detect one or more cardiac features (804). The operation of steps 802 and 84 may occur in a substantially similar fashion to steps 402 and 404 of FIG. 4, respectively. In some examples, the feature delineation performed by IMD 10 is adjusted for high sensitivity. For example, IMD 10 may implement a high-sensitivity automatic trigger algorithm to identify episodes of interest. In some examples, the feature delineation is configured to classify a segment of a cardiac electrogram of patient 4 as an episode of an arrhythmia of interest where the segment exhibits a RR rate greater than or equal to 90 beats per minute or less than 60 beats per minute, an RR variability greater than 50 milliseconds, or any morphology variation in the absence of noise. In some examples, the feature delineation is configured to classify a segment of a cardiac electrogram of patient 4 as an episode of an arrhythmia of interest where the segment is a non-noise, non-NSR duration.

IMD 10 determines whether arrhythmia dictionary 270 includes at least one entry (806). Each entry of arrhythmia dictionary 270 includes a classification defining an episode of arrhythmia as a specific type of arrhythmia, such as an episode of bradycardia, tachycardia, atrial fibrillation, ventricular fibrillation, or AV Block. Each entry further includes one or more cardiac features associated with an episode of cardiac arrhythmia of the corresponding classification.

In response to determining that arrhythmia dictionary 270 includes at least one entry (e.g., "YES" block of 806), IMD 10 applies machine learning system 250 to determine whether the cardiac features obtained via feature delineation are similar to cardiac features of an entry of arrhythmia dictionary 270 (816). In some examples, machine learning system 250 determines whether the cardiac features obtained via feature delineation are similar to cardiac features of the entry of arrhythmia dictionary 270 are dissimilar. In some examples, machine learning system 250 may not determine a specific type of arrhythmia, but detects any changes in the cardiac electrogram other than noise or NSR or an entry in arrhythmia dictionary 270.

In response to determining that the cardiac features obtained via feature delineation are similar to the cardiac features of an entry of arrhythmia dictionary 270 (e.g., "YES" block of 814), IMD 10 determines that the cardiac features obtained via feature delineation are indicative of an episode of arrhythmia of a classification that is the same as a classification of the entry of arrhythmia dictionary 270. In some examples, IMD 10 updates a counter of episodes of arrhythmia of the classification of the entry of arrhythmia dictionary 270 so as to track a total number of episodes of arrhythmia of that classification that have occurred in patient 4 (818). IMD 10 stores the value of the counter with the entry of arrhythmia dictionary 270 (820). After storing the value of the counter in arrhythmia dictionary 270, IMD 10 generates a report of the arrhythmia (810) and outputs the report to a clinician or monitoring center for review (812). The operation of steps 810 and 812 may occur in a substantially similar fashion to steps 610 and 612 of FIG. 6, respectively.

In response to determining that arrhythmia dictionary 270 does not include at least one entry (e.g., "NO" block of 806), or in response to determining that the cardiac features obtained via feature delineation are not similar to any entry in arrhythmia dictionary 270 (e.g., "NO" block of 814), then IMD 10 applies a machine learning model of machine learning system 250 to the cardiac electrogram data to characterize the episode of cardiac arrhythmia (808). For example, IMD 10 applies the machine learning model to verify that an episode of cardiac arrhythmia has occurred, and/or determines a classification of the episode of cardiac arrhythmia. In some examples, the machine learning model is a deep-learning model that characterizes the episode with "deep-features," e.g., the final deep-learning arrhythmia detection model states before soft-max classification).

IMD 10 stores the cardiac features in arrhythmia dictionary 270 as a new entry in arrhythmia dictionary 270 along with a value of a counter of the number of occurrences of the type of cardiac arrhythmia (e.g., "1" for the first occurrence corresponding to the new entry) (820). In some examples, IMD 10 stores deep features of the newly detected episode of arrhythmia in the entry. After creating the new entry and storing the value of the counter in arrhythmia dictionary 270, IMD 10 generates a report of the arrhythmia (810) and outputs the report to a clinician or monitoring center for review (812). For example, IMD 10 transmits cardiac electrogram data corresponding to the detected episode for expert review and confirmation by a clinician. The review is conducted by experts who can look beyond typical arrhythmias for signal changes associated with other patient characteristics such as drug change.

The following examples may illustrate one or more aspects of the disclosure.

Example 1

A method comprising: sensing, by a medical device comprising processing circuitry and a storage medium, cardiac electrogram data of a patient; performing, by the medical device, feature-based delineation of the sensed cardiac electrogram data to obtain cardiac features present in the cardiac electrogram data and indicative of an episode of arrhythmia in the patient; determining, by the medical device and based on the feature-based delineation, that the cardiac features satisfy threshold criteria for application of a machine learning model for verifying that the episode of arrhythmia has occurred in the patient; in response to determining that the cardiac features satisfy the threshold criteria for application of the machine learning model, applying, by the medical device, the machine learning model, trained using cardiac electrogram data for a plurality of patients, to the sensed cardiac electrogram data to verify, based on the machine learning model, that the episode of arrhythmia has occurred in the patient; and in response to verifying, by the machine learning model, that the episode of arrhythmia has occurred in the patient: generating, by the medical device, a report comprising an indication that the episode of arrhythmia has occurred in the patient and one or more of the cardiac features that coincide with the episode of arrhythmia; and outputting, by the medical device and for display, the report comprising the indication that the episode of arrhythmia has occurred in the patient and the one or more of the cardiac features that coincide with the episode of arrhythmia.

Example 2

The method of example 1, wherein the episode of arrhythmia in the patient is an episode of arrhythmia of a first classification in the patient, wherein applying the machine learning model to the sensed cardiac electrogram data to verify that the episode of arrhythmia has occurred in the patient comprises applying the machine learning model to the sensed cardiac electrogram data to verify that the episode of arrhythmia of the first classification has occurred in the patient, wherein the method further comprises applying the machine learning model to the sensed cardiac electrogram data to determine that an episode of arrhythmia of a second classification has occurred in the patient in response to determining, based on the feature-based delineation, that the episode of arrhythmia of the first classification has occurred in the patient, and wherein generating the report comprising the indication that the episode of arrhythmia has occurred in the patient and one or more of the cardiac features that coincide with the episode of arrhythmia comprises generating a report comprising an indication that the episode of arrhythmia of the first classification has occurred in the patient, an indication that the episode of arrhythmia of the second classification has occurred in the patient, and the one or more of the cardiac features that coincide with the episode of arrhythmia of the first classification.

Example 3

The method of any of examples 1 or 2, wherein the cardiac electrogram data comprises an electrocardiogram (ECG) of the patient.

Example 4

The method of any of examples 1 through 3, wherein performing feature-based delineation of the cardiac electrogram data to obtain the cardiac features present in the cardiac electrogram data comprises performing at least one of QRS detection, refractory processing, noise processing, or delineation of the cardiac electrogram data to obtain cardiac features present in the cardiac electrogram data.

Example 5

The method of any of examples 1 through 4, wherein applying the machine learning model to verify that the episode of arrhythmia has occurred in the patient comprises applying the machine learning model to verify that an episode of at least one of bradycardia, tachycardia, atrial fibrillation, ventricular fibrillation, or AV Block has occurred in the patient.

Example 6

The method of any of examples 1 through 5, wherein the cardiac features present in the cardiac electrogram data are one or more of RR intervals present in the cardiac electrogram data, a mean heartrate present in the cardiac electrogram data, a minimum heartrate present in the cardiac electrogram data, a maximum heartrate present in the cardiac electrogram data, a PR interval present in the cardiac electrogram data, a variability of heartrate present in the cardiac electrogram data, one or more amplitudes of one or more features of an electrocardiogram (ECG), or an interval between the or more features of the ECG.

Example 7

The method of any of examples 1 through 6, wherein the machine learning model trained using cardiac electrogram data for the plurality of patients comprises a machine learning model trained using a plurality of electrocardiogram (ECG) waveforms, each ECG waveform labeled with one or more episodes of arrhythmia of one or more classifications in a patient of the plurality of patients.

Example 8

The method of any of examples 1 through 7, wherein determining that the cardiac features satisfy the threshold criteria comprises determining that at least one of a physiological parameter of the patient or a parameter of the medical device satisfies the threshold criteria.

Example 9

The method of any of examples 1 through 8, wherein applying the machine learning model to the sensed cardiac electrogram data further comprises applying the machine learning model to at least one of: one or more characteristics of the sensed cardiac electrogram data correlated to arrhythmia in the patient; an activity level of the medical device; an input impedance of the medical device; or a battery level of the medical device.

Example 10

The method of any of examples 1 through 9, wherein applying the machine learning model to the sensed cardiac electrogram data comprises applying the machine learning model to the sensed cardiac electrogram data in response to determining that the cardiac features satisfy the threshold criteria and determining that a noise of at least one of the cardiac features is less than a predetermined threshold.

Example 11

The method of any of examples 1 through 10, wherein applying the machine learning model to the sensed cardiac electrogram data comprises applying the machine learning model to the sensed cardiac electrogram data in response to determining that the cardiac features satisfy the threshold criteria and determining that the patient is in a first posture state of a plurality of posture states.

Example 12

The method of any of examples 1 through 11, wherein applying the machine learning model to the sensed cardiac electrogram data comprises applying the machine learning model to the sensed cardiac electrogram data in response to determining that the cardiac features satisfy the threshold criteria and determining that the patient is in a first activity state of a plurality of activity states.

Example 13

The method of any of examples 1 through 12, wherein the method further comprises, in response to outputting the report comprising the indication that the episode of arrhythmia has occurred in the patient and the one or more of the cardiac features that coincide with the episode of arrhythmia: receiving, by the medical device and from a user, an adjustment to the feature-based delineation of the cardiac electrogram data; and performing, in accordance with the adjustment, feature-based delineation of the cardiac electrogram data to obtain second cardiac features present in the cardiac electrogram data.

Example 14

The method of any of examples 1 through 13, wherein the cardiac electrogram data of the patient comprises an electrocardiogram (ECG) of the patient, and wherein generating the report comprising the indication that the episode of arrhythmia has occurred in the patient and the one or more of the cardiac features that coincide with the episode of arrhythmia comprises: identifying a subsection of the ECG of the patient, wherein the subsection comprises ECG data for a first time period prior to the episode of arrhythmia, a second time period during the episode of arrhythmia, and a third time period after the episode of arrhythmia, and wherein a length of time of the ECG of the patient is greater than the first, second, and third time periods; identifying one or more of the cardiac features that coincide with the first, second, and third time periods; and including, in the report, the subsection of the ECG and the one or more of the cardiac features that coincide with the first, second, and third time periods.

Example 15

The method of any of examples 1 through 14, wherein determining, based on the feature-based delineation, that the cardiac features satisfy threshold criteria for application of the machine learning model for verifying that the episode of arrhythmia has occurred in the patient comprises determining, based on the feature-based delineation, that the cardiac features are indicative that an episode of arrhythmia of a first classification has occurred in the patient, and wherein applying the machine learning model to the sensed cardiac electrogram data to verify that the episode of arrhythmia has occurred in the patient comprises applying the machine learning model to the sensed cardiac electrogram data to verify the determination based on the feature-based delineation that the cardiac features are indicative of the episode of arrhythmia of the first classification.

Example 16

The method of any of examples 1 through 15, further comprising determining a burden of the episode of arrhythmia in the patient in response to verifying that the episode of arrhythmia has occurred in the patient, wherein the burden of the episode of arrhythmia in the patient comprises a ratio of a length of time of the episode of arrhythmia to a length of time during of monitoring of the patient by the medical device.

Example 17

The method of any of examples 1 through 16, wherein the method further comprises processing, by the medical device, the sensed cardiac electrogram data to generate filtered cardiac electrogram data, wherein applying the machine learning model to the sensed cardiac electrogram data to verify that the episode of arrhythmia has occurred in the patient comprises applying the machine learning model to the filtered cardiac electrogram data to verify that the episode of arrhythmia has occurred in the patient.

Example 18

The method of example 17, wherein processing the sensed cardiac electrogram data to generate the filtered cardiac electrogram data comprises: determining at least one of a period of time of a high level of activity of the patient or a period of time of highly-varying input impedance of the medical device; in response to determining the at least one of the period of time of the high level of activity of the patient or the period of time of highly-varying input impedance of the medical device, discarding at least a portion of the sensed cardiac electrogram data that coincides with the at least one of the period of time of the high level of activity of the patient or the period of time of highly-varying input impedance of the medical device to generate the filtered cardiac electrogram data.

Example 19

The method of example 18, wherein discarding at least a portion of the sensed cardiac electrogram data that coincides with the at least one of the period of time of the high level of activity of the patient or the period of time of highly-varying input impedance of the medical device comprises discarding one or more of a sensed input impedance of the medical device, a sensed activity level of the patient, or a sensed posture change of the patient that coincides with the at least one of the period of time of the high level of activity of the patient or the period of time of highly-varying input impedance of the medical device.

Example 20

The method of any of examples 1 through 19, further comprising: wherein applying the machine learning model to the sensed cardiac electrogram data to verify that the episode of arrhythmia has occurred in the patient comprises at least one of a first determination, based on the machine learning model, that the episode of arrhythmia has not occurred in the patient or a second determination, based on the machine learning model, that an episode of arrhythmia of a different type has occurred in the patient; in response to the at least one of the first determination and the second determination, updating, by the medical device, a counter of incorrectly detected episodes of arrhythmia in the patient; and in response to determining that a value of the counter is greater than a predetermined threshold, switching from performing feature-based delineation of the sensed cardiac electrogram data to obtain cardiac features present in the cardiac electrogram data and indicative of an episode of arrhythmia in the patient to applying a second machine learning model, trained using cardiac electrogram data for a plurality of patients, to the sensed cardiac electrogram data to obtain, based on the machine learning model, cardiac features present in the cardiac electrogram data and indicative of an episode of arrhythmia in the patient.

Example 21

The method of example 20, wherein sensing the cardiac electrogram data of the patient comprises sensing first cardiac electrogram data of the patient; and wherein the method further comprises: sensing, by the medical device, second cardiac electrogram data of the patient; applying the second machine learning model to the sensed second cardiac electrogram data to obtain, based on the machine learning model, second cardiac features present in the second cardiac electrogram data and indicative of a second episode of arrhythmia in the patient; in response to obtaining, by the second machine learning model, the second cardiac features indicative of the second episode of arrhythmia in the patient: generating, by the medical device, a second report comprising an indication that the second episode of arrhythmia has occurred in the patient and one or more of the second cardiac features that coincide with the second episode of arrhythmia; and outputting, by the medical device and for display, the second report comprising the indication that the second episode of arrhythmia has occurred in the patient and the one or more of the second cardiac features that coincide with the second episode of arrhythmia.

Example 22

The method of any of examples 21 or 22, further comprising: in response to determining that the value of the counter is greater than the predetermined threshold: updating, by the medical device, an estimate of power consumption by the medical device; and outputting, by the medical device and for display, the estimate of power consumption by the medical device.

Example 23

The method of any of examples 1 through 22, wherein the method further comprises processing, by the medical device, the sensed cardiac electrogram data to generate an intermediate representation of the sensed cardiac electrogram data, wherein applying the machine learning model, trained using cardiac electrogram data for the plurality of patients, to the sensed cardiac electrogram data to verify that the episode of arrhythmia has occurred in the patient comprises applying a machine learning model, trained using intermediate representations of cardiac electrogram data for a plurality of patients, to the intermediate representation of the sensed cardiac electrogram data and the cardiac features present in the cardiac electrogram data to verify that the episode of arrhythmia has occurred in the patient.

Example 24

The method of example 23, wherein processing the sensed cardiac electrogram data to generate the intermediate representation of the sensed cardiac electrogram data comprises at least one of: applying a filter to the sensed cardiac electrogram data; performing signal decomposition on the sensed cardiac electrogram data.

Example 25

The method of example 24, wherein performing signal decomposition on the sensed cardiac electrogram data comprises performing wavelet decomposition on the sensed cardiac electrogram data.

Example 26

A method comprising: sensing, by a medical device comprising processing circuitry and a storage medium, cardiac electrogram data of a patient; performing, by the medical device, feature-based delineation of the sensed cardiac electrogram data to obtain cardiac features present in the cardiac electrogram data; determining, by the medical device, a similarity of the obtained cardiac features to cardiac features of each entry of a plurality of entries of an arrhythmia dictionary of the medical device, wherein each entry of the plurality of entries of the arrhythmia dictionary comprises a classification of arrhythmia of a plurality of classifications of arrhythmia in the patient and cardiac features that demonstrate the classification of arrhythmia; in response to determining that the obtained cardiac features are not similar to the cardiac features of each entry of the plurality of entries of the arrhythmia dictionary, applying, by the medical device, a machine learning model, trained using cardiac electrogram data for a plurality of patients, to the sensed cardiac electrogram data to determine, based on the machine learning model, that an episode of arrhythmia of a first classification has occurred in the patient; and storing, by the medical device and in the arrhythmia dictionary, a first entry comprising the first classification of the episode of arrhythmia and the obtained cardiac features.

Example 27

The method of example 26, further comprising: after storing the entry comprising the first classification of the episode of arrhythmia and the obtained cardiac features: generating, by the medical device, a report comprising an indication that the episode of arrhythmia of the first classification has occurred in the patient and one or more of the obtained cardiac features that coincide with the episode of arrhythmia of the first classification; and outputting, by the medical device and for display, the report comprising the indication that the episode of arrhythmia of the first classification has occurred in the patient and the one or more of the obtained cardiac features that coincide with the episode of arrhythmia of the first classification.

Example 28

The method of any of examples 26 or 27, further comprising: sensing, by the medical device comprising processing circuitry and a storage medium, second cardiac electrogram data of a patient; performing, by the medical device, feature-based delineation of the sensed second cardiac electrogram data to obtain second cardiac features present in the second cardiac electrogram data; determining, by the medical device, the second cardiac features are similar to the cardiac features of the first entry of the plurality of entries of the arrhythmia dictionary of the medical device; in response to determining that the second cardiac features are similar to the cardiac features of the first entry of the plurality of entries of the arrhythmia dictionary: generating, by the medical device, a report comprising an indication that the episode of arrhythmia of the first classification has occurred in the patient and one or more of the second cardiac features that coincide with the episode of arrhythmia of the first classification; and outputting, by the medical device and for display, the report comprising the indication that the episode of arrhythmia of the first classification has occurred in the patient and the one or more of the second cardiac features that coincide with the episode of arrhythmia of the first classification.

Example 29

The method of any of examples 26 through 28, wherein determining a similarity of the obtained cardiac features to the cardiac features of each entry of the plurality of entries of the arrhythmia dictionary of the medical device comprises determining that an L1 distance of the obtained cardiac features is not similar to an L1 distance of the cardiac features of each entry of the plurality of entries of the arrhythmia dictionary of the medical device.

Example 30

The method of any of examples 26 through 28, wherein determining a similarity of the obtained cardiac features to the cardiac features of each entry of the plurality of entries of the arrhythmia dictionary of the medical device comprises determining that a difference between at least one parameter of the obtained cardiac features and at least one parameter of the cardiac features of each entry of the plurality of entries of the arrhythmia dictionary of the medical device is greater than a predetermined threshold.

Example 31

The method of any of examples 26 through 28, wherein determining a similarity of the obtained cardiac features to the cardiac features of each entry of the plurality of entries of the arrhythmia dictionary of the medical device comprises: applying a second machine learning model, trained using cardiac electrogram data for a plurality of patients, to the obtained cardiac features and the cardiac features of each entry of the plurality of entries of the arrhythmia dictionary of the medical device to determine, that the obtained cardiac features are not similar to the cardiac features of each entry of the plurality of entries of the arrhythmia dictionary of the medical device.

Example 32

The method of any of examples 26 through 31, further comprising: in response to determining that the obtained cardiac features are similar to cardiac features of a first entry of the plurality of entries of the arrhythmia dictionary of the medical device: updating, by the medical device, a counter of episodes of arrhythmia of a first classification defined by the first entry of the plurality of entries of the arrhythmia dictionary of the medical device; storing, by the medical device, the counter in the first entry of the plurality of entries of the arrhythmia dictionary of the medical device.

Example 33

The method of any of examples 26 through 32, further comprising determining, by the medical device, that the obtained cardiac features are not similar to a normal sinus rhythm (NSR) or noise of the patient, wherein applying the machine learning model to the sensed cardiac electrogram data to determine that the episode of arrhythmia of the first classification has occurred in the patient in response to determining that the obtained cardiac features are not similar to the cardiac features of each entry of the plurality of entries of the arrhythmia dictionary comprises applying the machine learning model to the sensed cardiac electrogram data to determine that the episode of arrhythmia of the first classification has occurred in the patient in response to determining that the obtained cardiac features are not similar to the cardiac features of each entry of the plurality of entries of the arrhythmia dictionary and in response to determining that the obtained cardiac features are not similar to the NSR of the patient.

In some examples, the techniques of the disclosure include a system that comprises means to perform any method described herein. In some examples, the techniques of the disclosure include a computer-readable medium comprising instructions that cause processing circuitry to perform any method described herein.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module, unit, or circuit for purposes of clarity, it should be understood that the techniques of this disclosure may be performed by a combination of units, modules, or circuitry associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing circuitry" as used herein may refer to any of the foregoing structure or any other physical structure suitable for implementation of the described techniques. Also, the techniques could be fully implemented in one or more circuits or logic elements.

Various examples have been described. These and other examples are within the scope of the following claims.

What is claimed is:

1. A method comprising:
   sensing, by a medical device comprising processing circuitry and a storage medium, cardiac electrogram data of a patient;
   determining that a portion of the cardiac electrogram data is indicative of an arrhythmia, wherein to determining that the portion of the cardiac electrogram data is indicative of the arrhythmia comprises performing, by the medical device, feature-based delineation of the sensed cardiac electrogram data to obtain cardiac features present in the cardiac electrogram data and indicative of an episode of arrhythmia in the patient;
   in response to determining that the portion of the cardiac electrogram data is indicative of the arrhythmia, determining, by the medical device and based on the feature-based delineation, whether the cardiac features indicative of the episode of arrhythmia satisfy threshold criteria for application of a machine learning model for verifying that the episode of arrhythmia has occurred in the patient;
   in response to determining that the cardiac features satisfy the threshold criteria for application of the machine learning model, applying, by the medical device, the machine learning model, trained using cardiac electrogram data for a plurality of patients, to the sensed cardiac electrogram data to verify, based on the machine learning model, that the episode of arrhythmia has occurred in the patient; and
   in response to verifying, by the machine learning model, that the episode of arrhythmia has occurred in the patient, transmitting, by the medical device to the external device, an indication that the episode of arrhythmia has occurred in the patient and one or more of the cardiac features that coincide with the episode of arrhythmia; and
   in response to determining that the cardiac features do not satisfy the threshold criteria for application of the machine learning model, transmitting the indication that the episode of the arrhythmia has occurred to the external device without using the machine learning model to verify the that the episode of the arrhythmia has occurred in the patient.

2. The method of claim 1,
   wherein the episode of arrhythmia in the patient is an episode of arrhythmia of a first classification in the patient,
   wherein applying the machine learning model to the sensed cardiac electrogram data to verify that the episode of arrhythmia has occurred in the patient comprises applying the machine learning model to the sensed cardiac electrogram data to verify that the episode of arrhythmia of the first classification has occurred in the patient,
   wherein the method further comprises applying the machine learning model to the sensed cardiac electrogram data to determine that an episode of arrhythmia of a second classification has occurred in the patient in response to determining, based on the feature-based delineation, that the episode of arrhythmia of the first classification has occurred in the patient, and
   wherein transmitting the indication that the episode of arrhythmia has occurred in the patient and one or more of the cardiac features that coincide with the episode of arrhythmia comprises generating a report comprising an indication that the episode of arrhythmia of the first classification has occurred in the patient, an indication that the episode of arrhythmia of the second classification has occurred in the patient, and the one or more of the cardiac features that coincide with the episode of arrhythmia of the first classification.

3. The method of claim 1, wherein determining that the cardiac features satisfy the threshold criteria comprises determining that at least one of a physiological parameter of the patient or a parameter of the medical device satisfies the threshold criteria.

4. The method of claim 1, wherein applying the machine learning model to the sensed cardiac electrogram data comprises applying the machine learning model to the sensed cardiac electrogram data in response to determining that the cardiac features satisfy the threshold criteria and determining that a noise of at least one of the cardiac features is less than a predetermined threshold.

5. The method of claim 1, wherein applying the machine learning model to the sensed cardiac electrogram data comprises applying the machine learning model to the sensed cardiac electrogram data in response to:
 determining that the cardiac features satisfy the threshold criteria; and
 determining that the patient is in a first posture state of a plurality of posture states.

6. The method of claim 1,
 wherein transmitting the indication that the episode of arrhythmia has occurred in the patient comprises generating a report comprising the indication that the episode of arrhythmia has occurred in the patient,
 wherein the cardiac electrogram data of the patient comprises an electrocardiogram (ECG) of the patient, and
 wherein generating the report comprising the indication that the episode of arrhythmia has occurred in the patient and the one or more of the cardiac features that coincide with the episode of arrhythmia comprises:
  identifying a subsection of the ECG of the patient, wherein the subsection comprises ECG data for a first time period prior to the episode of arrhythmia, a second time period during the episode of arrhythmia, and a third time period after the episode of arrhythmia, and wherein a length of time of the ECG of the patient is greater than the first, second, and third time periods;
  identifying one or more of the cardiac features that coincide with the first, second, and third time periods; and
  including, in the report, the subsection of the ECG and the one or more of the cardiac features that coincide with the first, second, and third time periods.

7. A medical device comprising:
 a storage medium; and
 processing circuitry operably coupled to the storage medium, and configured to:
  sense cardiac electrogram data of a patient;
  determine that a portion of the cardiac electrogram data is indicative of an arrhythmia, wherein to determine that the portion of the cardiac electrogram data is indicative of the arrhythmia, the processing circuitry is configured to perform feature-based delineation of the sensed cardiac electrogram data to obtain cardiac features present in the cardiac electrogram data and indicative of an episode of arrhythmia in the patient;
  in response to determining that the portion of the cardiac electrogram data is indicative of the arrhythmia, determine, based on the feature-based delineation, whether the cardiac features indicative of the episode of arrhythmia satisfy threshold criteria for application of a machine learning model for verifying that the episode of arrhythmia has occurred in the patient;
  in response to determining that the cardiac features satisfy the threshold criteria for application of the machine learning model, apply the machine learning model, trained using cardiac electrogram data for a plurality of patients, to the sensed cardiac electrogram data to verify, based on the machine learning model, that the episode of arrhythmia has occurred in the patient; and
  in response to verifying, by the machine learning model, that the episode of arrhythmia has occurred in the patient, transmit, to the external device, an indication that the episode of arrhythmia has occurred in the patient and one or more of the cardiac features that coincide with the episode of arrhythmia; and
  in response to determining that the cardiac features do not satisfy the threshold criteria for application of the machine learning model, transmit the indication that the episode of the arrhythmia has occurred to the external device without using the machine learning model to verify the that the episode of the arrhythmia has occurred in the patient.

8. The medical device of claim 7,
 wherein the episode of arrhythmia in the patient is an episode of arrhythmia of a first classification in the patient,
 wherein to apply the machine learning model to the sensed cardiac electrogram data to verify that the episode of arrhythmia has occurred in the patient, the processing circuitry is configured to apply the machine learning model to the sensed cardiac electrogram data to verify that the episode of arrhythmia of the first classification has occurred in the patient,
 wherein the processing circuitry is further configured to:
 apply the machine learning model to the sensed cardiac electrogram data to determine that an episode of arrhythmia of a second classification has occurred in the patient in response to determining, based on the feature-based delineation, that the episode of arrhythmia of the first classification has occurred in the patient,
 wherein to transmit the indication that the episode of arrhythmia has occurred in the patient and one or more of the cardiac features that coincide with the episode of arrhythmia, the processing circuitry is configured to generate a report comprising an indication that the episode of arrhythmia of the first classification has occurred in the patient, an indication that the episode of arrhythmia of the second classification has occurred in the patient, and the one or more of the cardiac features that coincide with the episode of arrhythmia of the first classification.

9. The medical device of claim 7, wherein to determine that the cardiac features satisfy the threshold criteria, the processing circuitry is configured to determine that at least one of a physiological parameter of the patient or a parameter of the medical device satisfies the threshold criteria.

10. The medical device of claim 7, wherein to apply the machine learning model to the sensed cardiac electrogram data, the processing circuitry is configured to apply the machine learning model to the sensed cardiac electrogram data in response to determining that the cardiac features satisfy the threshold criteria and determining that a noise of at least one of the cardiac features is less than a predetermined threshold.

11. The medical device of claim 7, wherein to apply the machine learning model to the sensed cardiac electrogram data, the processing circuitry is configured to apply the machine learning model to the sensed cardiac electrogram data in response to:
  determining that the cardiac features satisfy the threshold criteria; and
  determining that the patient is in a first posture state of a plurality of posture states.

12. The medical device of claim 7,
  wherein the processing circuitry is further configured to generate a report comprising the indication that the episode of arrhythmia has occurred in the patient,
  wherein the cardiac electrogram data of the patient comprises an electrocardiogram (ECG) of the patient, and
  wherein to generate the report comprising the indication that the episode of arrhythmia has occurred in the patient and the one or more of the cardiac features that coincide with the episode of arrhythmia, the processing circuitry is configured to:
    identify a subsection of the ECG of the patient, wherein the subsection comprises ECG data for a first time period prior to the episode of arrhythmia, a second time period during the episode of arrhythmia, and a third time period after the episode of arrhythmia, and wherein a length of time of the ECG of the patient is greater than the first, second, and third time periods;
    identify one or more of the cardiac features that coincide with the first, second, and third time periods; and
    include, in the report, the subsection of the ECG and the one or more of the cardiac features that coincide with the first, second, and third time periods.

13. The medical device of claim 7, wherein in response to transmitting the indication that the episode of arrhythmia has occurred in the patient and the one or more of the cardiac features that coincide with the episode of arrhythmia, the processing circuitry is configured to:
  receive, by the medical device and from a user, an adjustment to the feature-based delineation of the cardiac electrogram data; and
  perform, in accordance with the adjustment, feature-based delineation of the cardiac electrogram data to obtain second cardiac features present in the cardiac electrogram data.

14. The medical device of claim 7,
  wherein to determine, based on the feature-based delineation, that the cardiac features satisfy threshold criteria for application of the machine learning model for verifying that the episode of arrhythmia has occurred in the patient, the processing circuitry is configured to determine, based on the feature-based delineation, that the cardiac features are indicative that an episode of arrhythmia of a first classification has occurred in the patient, and
  wherein to apply the machine learning model to the sensed cardiac electrogram data to verify that the episode of arrhythmia has occurred in the patient, the processing circuitry is configured to apply the machine learning model to the sensed cardiac electrogram data to verify the determination based on the feature-based delineation that the cardiac features are indicative of the episode of arrhythmia of the first classification.

15. The medical device of claim 7, wherein the processing circuitry is configured to determine a burden of the episode of arrhythmia in the patient in response to verifying that the episode of arrhythmia has occurred in the patient, wherein the burden of the episode of arrhythmia in the patient comprises a ratio of a length of time of the episode of arrhythmia to a length of time during of monitoring of the patient by the medical device.

16. The medical device of claim 7,
  wherein the processing circuitry is configured to process the sensed cardiac electrogram data to generate filtered cardiac electrogram data,
  wherein to apply the machine learning model to the sensed cardiac electrogram data to verify that the episode of arrhythmia has occurred in the patient, the processing circuitry is configured to apply the machine learning model to the filtered cardiac electrogram data to verify that the episode of arrhythmia has occurred in the patient.

17. The medical device of claim 16, wherein to process the sensed cardiac electrogram data to generate the filtered cardiac electrogram data, the processing circuitry is configured to:
  determine at least one of a period of time of a high level of activity of the patient or a period of time of highly-varying input impedance of the medical device;
  in response to determining the at least one of the period of time of the high level of activity of the patient or the period of time of highly-varying input impedance of the medical device, discard at least a portion of the sensed cardiac electrogram data that coincides with the at least one of the period of time of the high level of activity of the patient or the period of time of highly-varying input impedance of the medical device to generate the filtered cardiac electrogram data.

18. The medical device of claim 17, wherein to discard at least a portion of the sensed cardiac electrogram data that coincides with the at least one of the period of time of the high level of activity of the patient or the period of time of highly-varying input impedance of the medical device, the processing circuitry is configured to discard one or more of a sensed input impedance of the medical device, a sensed activity level of the patient, or a sensed posture change of the patient that coincides with the at least one of the period of time of the high level of activity of the patient or the period of time of highly-varying input impedance of the medical device.

19. The medical device of claim 7, wherein applying the machine learning model to the sensed cardiac electrogram data to verify that the episode of arrhythmia has occurred in the patient comprises at least one of a first determination, based on the machine learning model, that the episode of arrhythmia has not occurred in the patient or a second determination, based on the machine learning model, that an episode of arrhythmia of a different type has occurred in the patient, wherein the processing circuitry is further configured to:
  in response to the at least one of the first determination and the second determination, update, by the medical device, a counter of incorrectly detected episodes of arrhythmia in the patient; and
  in response to determining that a value of the counter is greater than a predetermined threshold, switch from performing feature-based delineation of the sensed cardiac electrogram data to obtain cardiac features present in the cardiac electrogram data and indicative of an episode of arrhythmia in the patient to applying a second machine learning model, trained using cardiac electrogram data for a plurality of patients, to the sensed cardiac electrogram data to obtain, based on the machine learning model, cardiac features present in the cardiac electrogram data and indicative of an episode of arrhythmia in the patient.

20. The medical device of claim 7,
wherein the processing circuitry is configured to process the sensed cardiac electrogram data to generate an intermediate representation of the sensed cardiac electrogram data, wherein to apply the machine learning model, trained using cardiac electrogram data for the plurality of patients, to the sensed cardiac electrogram data to verify that the episode of arrhythmia has occurred in the patient, the processing circuitry is configured to apply a machine learning model, trained using intermediate representations of cardiac electrogram data for a plurality of patients, to the intermediate representation of the sensed cardiac electrogram data and the cardiac features present in the cardiac electrogram data to verify that the episode of arrhythmia has occurred in the patient.

21. The medical device of claim 7, wherein to determine, based on the feature-based delineation, whether the cardiac features indicative of the episode of arrhythmia satisfy the threshold criteria for application of the machine learning model for verifying that the episode of arrhythmia has occurred in the patient, the processing circuitry is configured to:
determine a difference between the cardiac features present in the cardiac electrogram data and a plurality of entries in an arrhythmia dictionary, wherein each entry of the plurality of entries of the arrhythmia dictionary comprises a classification of arrhythmia of a plurality of classifications of arrhythmia in the patient and cardiac features that are indicative of the classification of arrhythmia; and
in response to determining that the difference between the between the cardiac features present in the cardiac electrogram data and a plurality of entries in an arrhythmia dictionary is greater than a predetermined threshold, determine that the cardiac features indicative of the episode of arrhythmia satisfy the threshold criteria for application of the machine learning model.

22. The medical device of claim 7, wherein to determine, based on the feature-based delineation, whether the cardiac features indicative of the episode of arrhythmia satisfy the threshold criteria for application of the machine learning model for verifying that the episode of arrhythmia has occurred in the patient, the processing circuitry is configured to:
determine a difference between the cardiac features present in the cardiac electrogram data and a plurality of entries in an arrhythmia dictionary, wherein each entry of the plurality of entries of the arrhythmia dictionary comprises a classification of arrhythmia of a plurality of classifications of arrhythmia in the patient and cardiac features that are indicative of the classification of arrhythmia; and
in response to determining that the difference between the between the cardiac features present in the cardiac electrogram data and a plurality of entries in an arrhythmia dictionary is less than a predetermined threshold, determine that the cardiac features indicative of the episode of arrhythmia do not satisfy the threshold criteria for application of the machine learning model.

* * * * *